US010093938B2

(12) United States Patent
Ikushima et al.

(10) Patent No.: US 10,093,938 B2
(45) Date of Patent: Oct. 9, 2018

(54) REGULATED SWITCH FOR GENE EXPRESSION

(71) Applicant: The Johns Hopkins University, Baltimore, MD (US)

(72) Inventors: Shigehito Ikushima, Towson, MD (US); Jef Boeke, New York, NY (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/118,508

(22) PCT Filed: Feb. 19, 2015

(86) PCT No.: PCT/US2015/016619
§ 371 (c)(1),
(2) Date: Aug. 12, 2016

(87) PCT Pub. No.: WO2015/175074
PCT Pub. Date: Nov. 19, 2015

(65) Prior Publication Data
US 2017/0051294 A1 Feb. 23, 2017

Related U.S. Application Data

(60) Provisional application No. 61/941,551, filed on Feb. 19, 2014.

(51) Int. Cl.
*C12N 15/81* (2006.01)
*C12N 15/63* (2006.01)

(52) U.S. Cl.
CPC ............. *C12N 15/81* (2013.01); *C12N 15/63* (2013.01); *C12N 15/635* (2013.01)

(58) Field of Classification Search
None
See application file for complete search history.

(56) References Cited

U.S. PATENT DOCUMENTS

| 5,891,718 A | 4/1999 | Hobart |
| 6,203,976 B1 | 3/2001 | Foulkes et al. |
| 2005/0034187 A1 | 2/2005 | Golovko et al. |

FOREIGN PATENT DOCUMENTS

WO 1992012635 8/1992

OTHER PUBLICATIONS

Aramaki et al "Evidence for Autoregulation of camR, Which Encodes a Repressor for the Cytochrome P-450cam Hydroxylase Operon on the Pseudomonas putida CAM Plasmid" (Journal of Bacteriology, Dec. 1993, vol. 175, No. 24, pp. 7828-7833).*
Tongyoo Thesis entitled: "Physical and functional analysis of genes from the CAM catabolic plasmid encoding probable steps in the catabolism of camphor" (Nov. 2002).*
Aparicio, O. et al. Modifiers of position effect are shared between telomeric and silent mating-type loci in S. cerevisiae. Cell 66: 1279-1287.
Aramaki, H., et al. 1993. Evidence for autoregulation of camR, which encodes a repressor for the cytochrome P-450cam hydroxylase operon on the pseudomonas putida CAM plasmid. J. Bacteriol. 175: 7828-7831.
Aramaki, H. et al, 2011 Formation of repressorinducer-operator ternary complex: Negative cooperativity of D-camphor binding to CamR. Genes Cells 16: 1200-1207.
Baron, U., et al.1997 Tetracycline-controlled transcription m eukaryotes: Novel transactivators with graded transactivation potential. Nucleic Acids Res. 25: 2723-2729.
Braselmann S., et al. 1993 A selective transcriptional induction system for mammalian cells based on Gal-4-estrogen receptor fusion proteins. Proc. Natl. Acad. Sci. U.S.A. 90: 1657-1661.
Engler, C., et al., 2011 Generation of families of construct variants using golden gate shuffling. Methods Mol. Biol. 729: 167-181.
Fujita, M., et al., 1993 Transcription of the cam operon and camR genes inpseudomonas putida PpG1. J. Bacteriol. 175: 6953-6958.
Gari, E., L. et al.,1997 A set of vectors with a tetracycline regulatable promoter system for modulated gene expression in *Saccharomyces cerevisiae*. Yeast 13: 837-848.
Kalderon, D., et al., 1984 A short amino acid sequence able to specify nuclear location. Cell 39: 499-509.
Maya, D., et al., 2008 Systems for applied gene control in *Saccharomyces cerevisiae*. Biotechnol. Lett. 30: 979-987.
Mitchell, L. A., et al, 2013 Multichange isothermal mutagenesis: A new strategy for multiple site-directed mutations in plasmid DNA. ACS Synth. Biol. 2: 473-477.
Richardson, S. M., et al., 2006 GeneDesign: Rapid, automated design of multikilobase synthetic genes. Genome Res. 16: 550-556.
Tsuge, K., et al., 2003 One step assembly of multiple DNA fragments with a designed order and orientation in bacillus subtilis plasmid. Nucleic Acids Res. 31: e133.
Aramaki, H. et al. Residues Important for the Function of a Multihelical DNA Binding Domain in the New Transcription Factor Family of Cam and Tet Repressors. Protein Engineering. 1995, vol. 8, No. 12, pp. 1259-1266.
Gossen, M. et al . Tight Control of Gene Expression in Mammalian Cells by Tetracycline-Responsive Promoters. Proc. Natl. Acad. Sci. USA. Jun. 1992, vol. 89, pp. 5547-5551.

(Continued)

*Primary Examiner* — Catherine S Hibbert
(74) *Attorney, Agent, or Firm* — Johns Hopkins Technology Ventures

(57) ABSTRACT

A system for controlling gene expression in yeast comprises a repressible gene expression plasmid that has a regulator binding sequence for camR and a target gene sequence. The system also includes a transcription enhancer expression plasmid; wherein said transcriptional activator protein binds to the regulator binding sequence in the absence of a transcriptional inhibitor. The system is used in a method for controlling expression of the target gene through the use of camphor. The target gene is expressed in the absence of camphor but unexpressed if camphor is added to a solution of cells containing the plasmids.

15 Claims, 9 Drawing Sheets

Specification includes a Sequence Listing.

(56) References Cited

OTHER PUBLICATIONS

Aramaki, H, et al. Nucleotide sequence of the gene encoding a repressor for the cytochrome P-450cam hydroxylase operon on the Pseudomonas putida CAM plasmid. Biochimie. 1994;76(1):63-70. PubMed PMID: 8031906.
Aramaki, H, et al. Heterologous expression of the cytochrome P450cam hydroxylase operon and the repressor gene of Pseudomonas putida in *Escherichia coli*. FEMS Microbiol Lett. Oct. 15, 1994;123(1-2):49-54. PubMed PMID: 7988898.
Duraiswami, S., and M. K. Subramaniam, 1952 Studies on the mutagenic action of chemical and physical agencies on yeasts. P. Indian Acad. Sci. B 35: 155-166.
Gomes-Carniero, M. R., et al. 1998 Mutagenicity testing (+/−)-camphor, 1,8-cineole, citral, citronellal, (-)-mentol and terpineol with the Salmonella/microsome assay. Mutat. Res. 416: 129-136.
Malinovska, L., et al. 2012 Molecular chaperones and stress-inducible protein-sorting factors coordinate the spatiotemporal distribution of protein aggregates. Mol. Biol. Cell 23: 3041-3056.
Tkach, J. M. et al, 2012 Dissecting DNA damage response pathways by analysing protein localization and abundance changes during DNA replication stress. Nat. Cell Biol. 14: 966-976.
Wu, J., et al. 2004 Global analysis of nutrient control of gene expression in *Saccharomyces cerevisiae* during growth and starvation. Proc. Natl. Acad. Sci. U. S. A. 101: 3148-3153.
Aramaki, H, et al. Purification and characterization of a cam repressor (CamR) for the cytochrome P-450cam hydroxylase operon on the Pseudomonas putida CAM plasmid. J Bacteriol. Jun. 1995;177(11):3120-7.
Aramaki, H, et al. In vitro transcriptional analysis of the cytochrome P-450cam hydroxylase operon. Biol Pharm Bull. Oct. 1999;22(10):1110-2.

\* cited by examiner

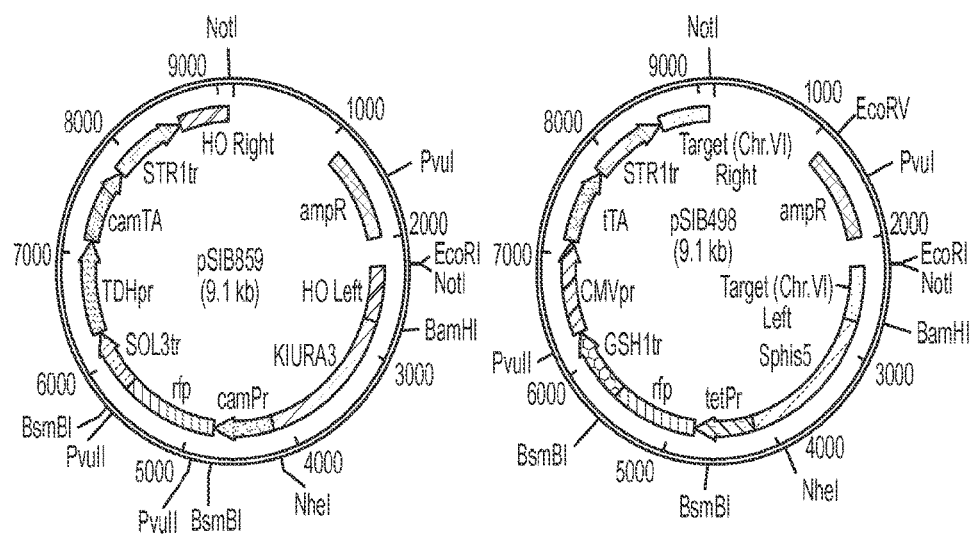
FIG. 6A  FIG. 6B
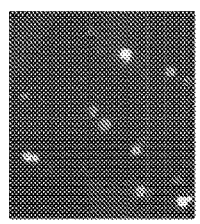 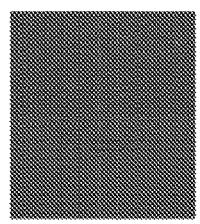 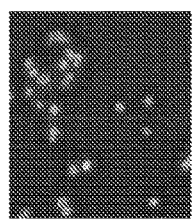 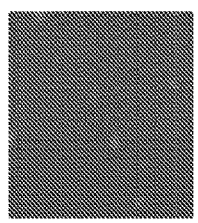
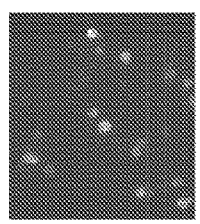 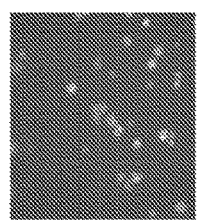 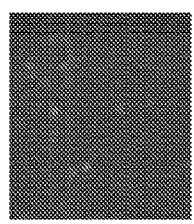 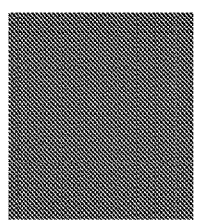
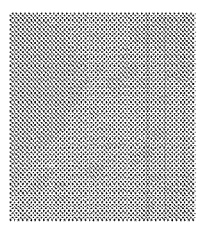 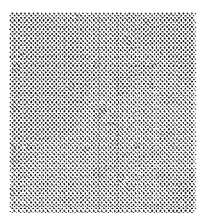 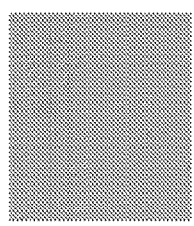 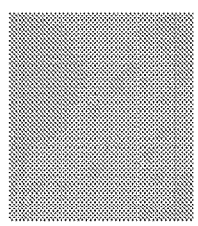
FIG. 6C  FIG. 6D  FIG. 6E  FIG. 6F

REGULATED SWITCH FOR GENE EXPRESSION

CROSS-REFERENCE TO RELATED APPLICATIONS

This application claims priority from U.S. Provisional Application Ser. No. 61/941,551, entitled A TIGHTLY CONTROLLED OFF SWITCH FOR *SACCHAROMYCES CEREVISIAE* REGULATED BY CAMPHOR and filed on Feb. 19, 2014, the specification of which is incorporated herein by reference in its entirety.

STATEMENT OF GOVERNMENT RIGHTS

This invention was made with government support under N66001-12-C-4020 awarded by Defense Advanced Research Projects Agency (DARPA). The government has certain rights in the invention.

TECHNICAL FIELD

This invention relates to the field of biotechnology and more specifically to a system and method for control of gene expression.

BACKGROUND ART

Budding yeast *Saccharomyces cerevisiae* ("*S. cerevisiae*") is one of the most important organisms in biotechnology. An enormous number of studies have been performed, and currently there are two types of regulated promoters in the yeast. The first type is an innate yeast promoter, such as the set of GAL promoters, expression of which is repressed by glucose and activated by galactose. The GAL1 promoter is used in many cases because its induction ratio is very high, but the high concentration of galactose required in the system can be problematic. Apart from the GAL promoters, researchers can use repressive promoters from the MET3 gene (negatively regulated by methionine) and PHO5 (negatively regulated by inorganic phosphate). However, the use of these promoters has multiple potentially undesirable effects on metabolism and host gene transcription and, importantly, can lead to a slow growth rate or a high cost incompatible with biotechnological applications. In other words, they are suboptimal, especially for biotechnology applications.

The other type of promoters consists of synthetic functional units derived from other organisms, such bacteria and viruses. One of the most studied switches, called the Tet system, has been applied to regulate expression in yeast. In that system, a transcription factor, the TetR protein from *Escherichia coli* ("*E. coli*"), can bind to its operator sequence depending on the presence or absence of tetracycline or derivative compounds such as anhydrotetracycline or doxycycline. However, use of the antibiotics hinders large-volume fermentation in industry because of their expense and moreover the use of the antibiotics is undesirable from a regulatory standpoint. Thus, a low-cost alternate system is desirable to facilitate regulated protein and pathway expression for yeast fermentation in a large-scale of millions of liters at one time. In addition, an increase in the number of available ligand-activated switches provides more options for fundamental and applied studies. The vast number of known and unknown promoters, however, makes it very difficult to identify possible new candidates that would overcome the problems of the existing systems.

Previous articles have described an autoregulated camphor oxidation operon in the 240-kb plasmid PpG1 from *Pseudomonas putida* ("*P. putida*"). Expression of the enzymes in this operon is induced by the presence of camphor, because a TetR-homolog transcription factor, camR, when bound to camphor dissociates from the bound operator. Notably, camphor is very inexpensive and widely used, even in human daily life. None of the literature, however, has shown that the autoregulated camphor operon of *P. putida* would be active in *S. cerevisiae* or other systems.

DISCLOSURE OF THE INVENTION

A system for controlling gene expression in yeast comprises a repressible gene expression plasmid that has a regulator binding sequence for camR and a target gene sequence. The system also includes a transcription enhancer expression plasmid; wherein said transcriptional activator protein binds to the regulator binding sequence in the absence of a transcriptional inhibitor. The system is used in a method for controlling expression of the target gene through the use of camphor. The target gene is expressed in the absence of camphor but unexpressed if camphor is added to a solution of cells containing the plasmids.

A recombinantly engineered cell comprises a recombinant sequence for expression of a camphor dependent transcription activator and a recombinant gene expression sequence comprising a camphor operator sequence, which is capable of binding the camphor dependent transcription activator to prevent gene expression when the cell is placed in media containing camphor. The gene of interest is expressed constitutively in the absence of camphor.

A transcription enhancer expression plasmid comprises a nucleic acid sequence encoding a camR transcription regulator domain, and a transcriptional activation domain, wherein the resulting camR transcription regulator domain and transcriptional activation domain are operatively connected and form a cam-TA. A recombinantly expressed transcriptional enhancer comprises a camR transcription regulator domain and a transcriptional activator domain. A repressible gene expression plasmid comprises a regulator binding sequence capable of binding a camR activator in the absence of camphor, which binding leads to expression of the target gene downstream from the regulator binding sequence.

A system for expression control of at least two peptide molecules comprises a first peptide molecule expressed under control of a first repressible promoter, and a second peptide molecule expressed under control of a transcriptional enhancer comprising a camR transcription regulator domain and a transcriptional activator domain, wherein the at least two peptide molecules are capable of being expressed in a eukaryotic cell.

BRIEF DESCRIPTION OF THE DRAWINGS

The above and other features, aspects, and advantages of the present invention are considered in more detail, in relation to the following description of embodiments thereof shown in the accompanying drawings, in which:

FIG. 6. Independent regulation of fluorescent reporters, RFP and GFP, with camphor-Off and Tet-Off systems. (A) pSIB859 can be used for integrating the camphor-Off system at a single transformation. Its derivative plasmid pSIB872 carries mCherry as a reporter. (B) Plasmid pSIB498 for the Tet-Off system. Its derivative pSIB527 carries gfp as a reporter. (C)-(F) Strain BY-TeCaOFF carries both pSIB872 and pSIB527. Cell images in SC medium (C), SC with camphor (D), SC with Dox (E), and SC with camphor and Dox. The top, middle, and bottom rows represent images of RFP, GFP, and DIC, respectively. Strain BY-TeCaOFF was grown for 1 day in SC medium with the indicated compounds. Camphor and Dox were supplemented at 25 µM each.

BEST MODE(S) FOR CARRYING OUT THE INVENTION

Figure 1A:
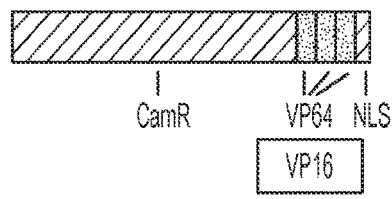
FIG. 1. Diagram of camphor-Off switch components in *S. cerevisiae*. (A) camR-based transcriptional regulator (cam-TA) consisting of camR, a trimeric repeat of VP16 transcription activation domain, and SV40 nuclear localization signal (NLS). (B) Plasmid pSIB619 for expressing cam-TA. NotI digestion releases an integration cassette ready to integrate into a neutral site in chromosome XI. (C) Architecture of a promoter designed to regulate the expression of genes of interest. The promoter camPr consists of the ADH1 transcriptional terminator, six repeats of the camR operator (camO), and the CYC1 minimal promoter, CYC1pr(min). (D) Plasmid pSIB426 (SEQ ID No. 1), harboring a GFP reporter. A similar plasmid pSIB791, contains an ADE2 (SEQ ID No. 10) gene in place of the gfp reporter in pSIB426.
Figure 1C:
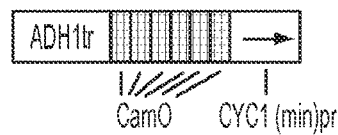
Figure 1B:
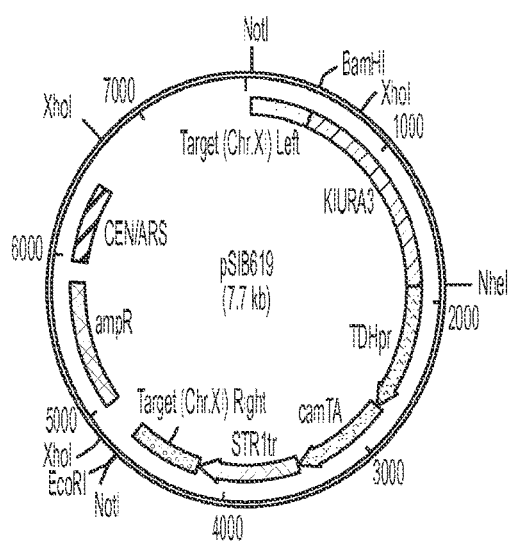
Figure 1D:
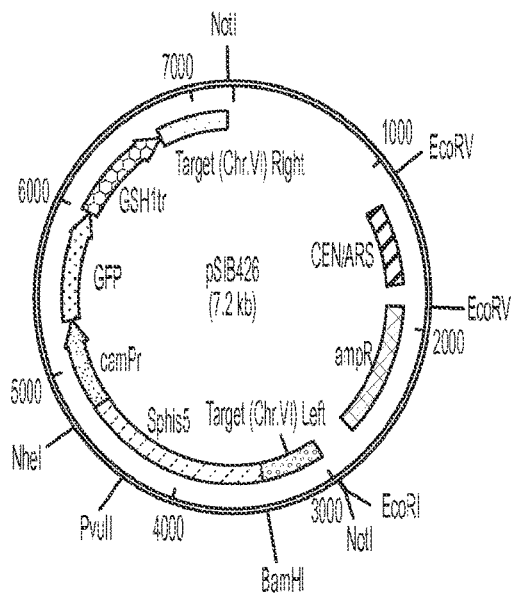

The invention summarized above may be better understood by referring to the following description. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

There are enormously increasing needs for effective switches in biotechnology-related fields. The camphor-Off system described in this application can realize a tight regulation of transcription in yeast with camphor, an inexpensive waste product of the Kraft pulping process. This camphor-Off system provides a switch that turns off the expression of genes of interest only by supplementing camphor in a micromolar-order concentration that does not have a big impact on yeast physiology, differently from most of other repressive switches previously developed, such as the MET3 and PHO5 promoters. In other words, this new system can be useful in many contexts, not only in laboratories, but also in industry where kilo- to mega-liter scale fermentation are often performed. From this point of view, the camphor-Off switch is expected to be one of the most valuable switches to regulate gene expression.

In one embodiment of the present invention, a nucleic acid sequence is disclosed that comprises a promoter containing a regulator binding sequence, also known as a camR binding operator, wherein the regulator binding sequence is capable of binding a camR transcriptional activator (cam-TA) in the absence of camphor, which binding leads to expression of a target gene downstream from the regulator binding sequence. When camphor is introduced, expression of the downstream gene is turned off.

A further embodiment discloses a nucleic acid sequence for a yeast transcriptional activator protein. The nucleic acid encodes at least two components: a nucleic acid sequence encoding camR and a transcriptional activation domain. In some embodiments, the nucleic acid will also include a nuclear localization signal. The components are expressed as a hybrid peptide wherein the resulting camR, the transcriptional activation domain and, when present, the nuclear localization signal are operatively connected and form a transcriptional activator cam-TA, which is sensitive to camphor. In the presence of camphor, the cam-TA is not able to bind the camR binding operator and, thus, expression of the downstream gene is turned off.

The term "vector" is used to describe a nucleic acid molecule capable of expressing a desired peptide or protein construct in a given organism. A recombinant "vector" brings together various elements of the peptide or protein to be expressed, which provides the properties described in this application. In general, vectors used in recombinant DNA techniques are referred to as "plasmids" or double stranded DNA molecules that are capable of replicating and utilize the cellular machinery of their host to express their particular target peptide or protein. In some instances, plasmids are used to incorporate a desired gene sequence in a particular site of a chromosome of a eukaryotic cell, such as a *S. cerevisiae* cell.

In one preferred embodiment, a system for controlling gene expression in yeast comprises a repressible gene expression plasmid having a regulator binding sequence sequence for camR and a target gene sequence, and a transcription enhancer expression plasmid; wherein said transcriptional activator protein binds to the regulator binding sequence in the absence of a transcriptional inhibitor. The repressible gene expression plasmid may include a regulator binding sequence capable of binding a camR activator in the absence of camphor, which binding leads to expression of the target gene downstream from the regulator binding sequence. The repressible gene expression plasmid further comprises a sequence for the target gene as shown in the examples below. The target gene expression may also include a transcription terminator sequence, e.g., ADH1, located upstream of the regulator binding sequence. A person of ordinary skill in the art would recognize that the term "upstream" means that the terminator sequence is placed before the regulator binding sequence.

The regulator binding sequence is at least one copy the sequence of camO (SEQ ID No. 17). In some embodiments, multiple copies of the camO (SEQ ID No. 17) are included, which may assist in ensuring that the regulator attaches to the binding sequence to promote transcription. In a preferred embodiment, the regulator binding sequence comprises at least six copies of the camO sequence (SEQ ID No. 17). The repressible gene expression plasmid also includes a promoter downstream from said regulator binding sequence. In a preferred embodiment, the promoter lacks an upstream activating sequence in order to prevent constitutive expression of the gene in the absence of the regulator. One preferred embodiment, as described below is CYC1.

The transcription enhancer expression plasmid that is part of the system includes a nucleic acid sequence encoding camR, and a transcriptional activation domain, wherein the resulting camR, transcriptional activation domain are operatively connected and form a cam-TA (camphor transcription activator). In one preferred embodiment, the transcriptional activation domain comprises at least one VP16 tandem repeat, in other embodiments, it may include three or more VP16 tandem repeats. One additional component in some embodiments is a nuclear localization signal such as the nuclear localization signal is derived from SV40 described in more detail below. In yet a further embodiment, the plasmid may include a glycolytic promoter sequence, such as the sequence for TDH1 as described below.

In yet a preferred embodiment, a recombinantly engineered eukaryotic cell, e.g., S. cerevisiae, is designed to include a recombinant sequence for expression of a camphor dependent transcription activator and a recombinant gene expression sequence comprising a camphor operator sequence, which is capable of binding the camphor activator to prevent gene expression when the cell is placed in media containing camphor. The recombinant gene expression sequence includes a regulator binding sequence capable of binding a camR activator in the absence of camphor and a target gene sequence, which binding leads to expression of the target gene downstream from the regulator binding sequence. The recombinant gene expression sequence further includes a transcription terminator sequence, e.g., ADH1, located upstream of the regulator binding sequence. The regulator binding sequence also includes at least one copy, preferably at least six copies, of the sequence of camO (SEQ ID No. 17). In a further embodiment, regulator binding sequence has a promoter, preferably lacking an upstream activating sequence, downstream from said regulator binding sequence, e.g., CYC1.

The recombinantly engineered cell also includes the sequence for expression of a camphor activator. The camphor activator includes a nucleic acid sequence encoding camR, and a transcriptional activation domain, wherein the resulting camR, transcriptional activation domain are operatively connected and form a cam-TA. The transcriptional activation domain comprises at least one, preferably three copies, of a VP16 tandem repeat. In a further embodiment, the camphor activator also includes a nuclear localization signal, which in some embodiments is derived from SV40, it is understood that other nuclear localization signals known in the art may be utilized. In some further embodiments, the transcriptional activation domain includes a glycolytic promoter sequence such as TDH1.

In yet a further embodiment, a recombinantly expressed transcriptional enhancer has a camR transcription regulator domain and a transcriptional activator domain. In a preferred embodiment, the transcriptional activator is VP16. In a further embodiment, a nuclear localization signal is included in the transcriptional enhancer.

A system for expression control of at least two peptide molecules consists of a first peptide molecule expressed under control of a first repressible promoter, and a second peptide molecule expressed under control of a transcriptional enhancer comprising a camR transcription regulator domain and a transcriptional activator domain, wherein the at least two peptide molecules are capable of being expressed in a eukaryotic cell, e.g., S. cerevisiae.

Construction of a CamR-Based Transcriptional Regulator for S. cerevisiae

As shown in FIG. 1 (A) the yeast transcriptional regulator named cam-TA consisting of Pseudomonas putida camR (GenBank BAA03510.1), three tandem repeats of a VP16 transcriptional activation domain derived from herpes simplex virus Type 1, and a nuclear localization signal (NLS) from SV40 and codon-optimized using GeneDesign. The particular construct of FIG. 1 (A) is pSIB619 and comprises the sequence of cam-TA (CDS) that consisted of camR (1-558) (SEQ ID No. 2), VP16 (559-684) (SEQ ID No. 3), and a nuclear localization signal (NLS: 685-708) (SEQ ID No. 4). The cam-TA was flanked by convergent BsmBI sites, and the overhangs generated by cutting are pAATG (5' side) and pTGAG (3' side). The sequence also includes the TDH1 promoter (SEQ ID No. 5) and the STR1 terminator (SEQ ID No. 6). An intrinsic BsmBI recognition site was previously removed by recoding. In one embodiment, the glycolytic promoter TDH1 was used to drive cam-TA expression (FIG. 1B). A person of ordinary skill would recognize that other transcriptional activation domains, nuclear localization signals, and codon-optimization can be utilized. It is also understood that sequences that are "substantially identical" homologs of the above-referenced sequence can be utilized in association with the present system.

A person of ordinary skill in the art understands that "substantially identical" homologs of the sequences described herein constitute exemplary embodiments of the present invention. Two amino acid sequences are "substantially identical" if (i) have only conservative amino acid substitutions that do not significantly affect the folding activity of the resulting polypeptide; (ii) the number of gaps between or insertions in, deletions of and substitutions of, is no more than 10%, preferably 5%, of the number of amino acid residues that occur over the length of the shortest of two aligned sequences; or (ii) no more than 30%, preferably 20%, more preferably 15%, or 10%, of the amino acid residues vary between the two sequences. Other methods as described by Houston et al. in United States Application Publication Number US2003/0161809A1 may also be used to determine whether two sequences are substantially identical.

Construction of a Camphor Responsive Promoter Using GFP as a Reporter

CamR, a component of cam-TA, binds to a specific sequence, 5'-CAGGCTCTATATCTGCGATATACTGAG-CAT (camO) (SEQ. ID No. 18). A gene of interest is placed downstream of the camO binding sequence as recognized by a person of ordinary skill in the art. In one preferred embodiment, as shown in FIG. 1 (C), six repeats of the operator sequence (camO) separated by a junction sequence 5'-CCCCC between the alcohol dehydrogenase ADH1 terminator and a CYC1 (cytochrome c) promoter from which the endogenous UAS (upstream activating sequence) had been removed. The architecture, consisting of a terminator, an operator, and a UAS-less promoter, was analogous to a promoter used in the yeast Tet-system. The camO-containing promoter (camPr) was designed to regulate expression of genes of interest. One preferred embodiment as shown in FIG. 1 (D) provides a vector plasmid pSIB426 (SEQ ID No. 1) to insert the camPr into the yeast chromosome. The pSIB426 plasmid comprises (A) Sequence of a promoter (camPr) (SEQ ID No. 7) consisting of ADH1 terminator (1-207), camR operator (camO: 208-430), and CYC1 minimal promoter (431-577); (B) gfp gene (CDS) (SEQ ID No. 8); and (C) GSH1 terminator (SEQ ID No. 9).

Performance of the New Switch—GFP as a Reporter

Figure 2B:
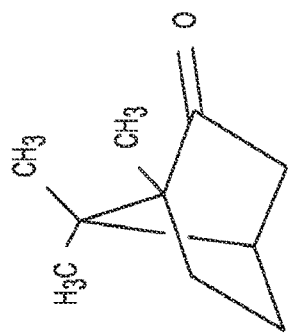
FIG. 2. Schematic diagram of the camphor-Off switch system (A) and chemical structure of D-camphor (B).
Figure 2A:
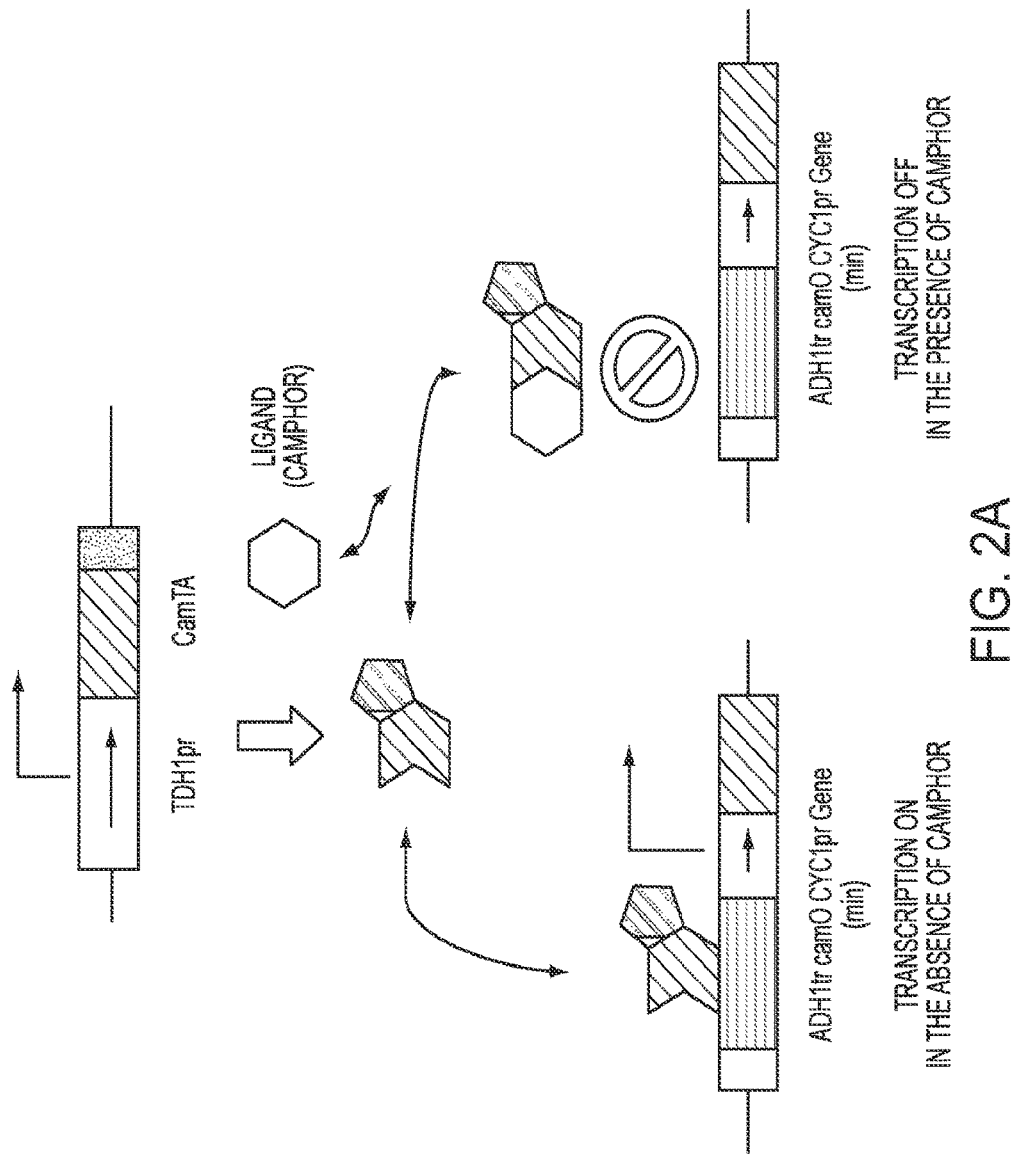

FIG. 2 shows the performance of the camphor-Off system by combining the two components, cam-TA and camPr, described in the previous sections. In an effective system, we expected that a reporter gene under the control of camPr would express in the absence of camphor, a ligand of camR, but that the expression of the reporter would be repressed by a certain amount of camphor (FIG. 2). To evaluate the performance of the system, we used GFP as a reporter.

Figure 3A:
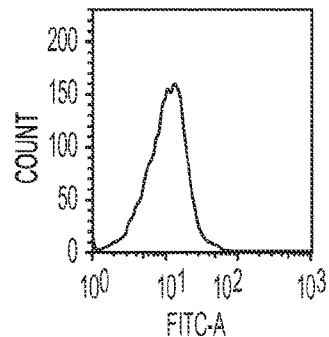
FIG. 3. Characteristics of the camphor-Off switch. (A-F) Cells were cultured in SC medium without camphor (A, B, C) and with 100 µM (D), 25 µM (E), and 13 µM (F) of camphor. The strains were BY4741 (A), camG (B), and camG-TA (C-F). FITC-A shows the intensity of GFP fluorescence. (G) Time course of GFP fluorescence. The y-axis is equal to mean values of fluorescence out of 10,000 counts. Open and closed squares represent the camG-TA cells grown in the absence or presence of camphor respectively (N=5). Open circle shows BY4741 grown without camphor (N=3). Error bars reflect standard deviations.
Figure 3B:
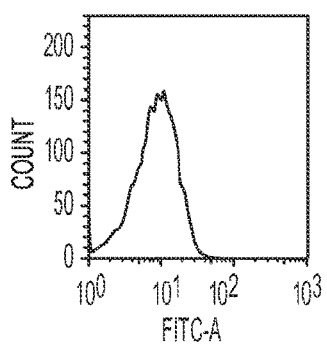
Figure 3C:
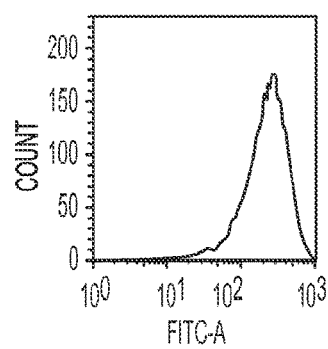
Figure 3D:
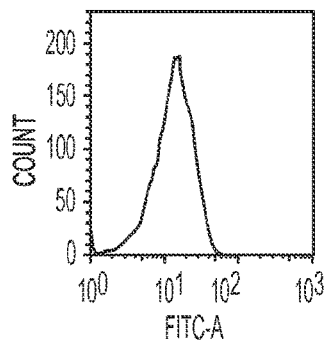
Figure 3E:
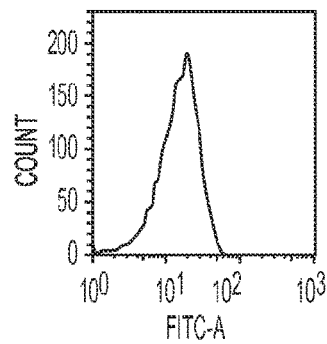
Figure 3F:
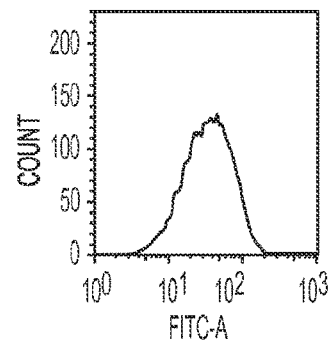

The intensity of GFP did not vary between the host strain BY4741 and a control strain camG containing the camPr-gfp expression cassette but lacking the cam-TA construct (Table 1 and FIG. 3AB). However, another strain camG-TA that was constructed by introducing the cam-TA-gfp expression cassette into the cam-TA strain produced significant amounts of GFP (FIG. 3C). From this, we conclude that cam-TA binds to camO and can activate the transcription of the reporter gene gfp. We then cultured the camG-TA strain in medium containing different camphor concentrations. The GFP signal drastically decreased in the presence of ≥25 μM of camphor (FIG. 3D-F), indicating that the ligand camphor dissociated the binding between cam-TA and camO. The lack of overlap between the two peaks (zero vs 25 μM camphor) suggests that switch states will be stable.

Figure 3G:
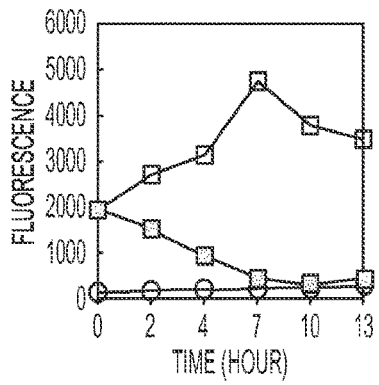

Subsequently, the kinetics of the system was investigated using the camG-TA strain. The intensity of GFP began high in the absence of camphor, whereas it went to almost the same level to that of BY4741 over a 7-hour period in the presence of camphor (FIG. 3G). It was reasonable that the signal did not disappear just after the addition of camphor because native GFP has a half-life of about 7 hours in yeast.

Camphor-Off System with an ADE2 Reporter

Figures 4A, 4B:
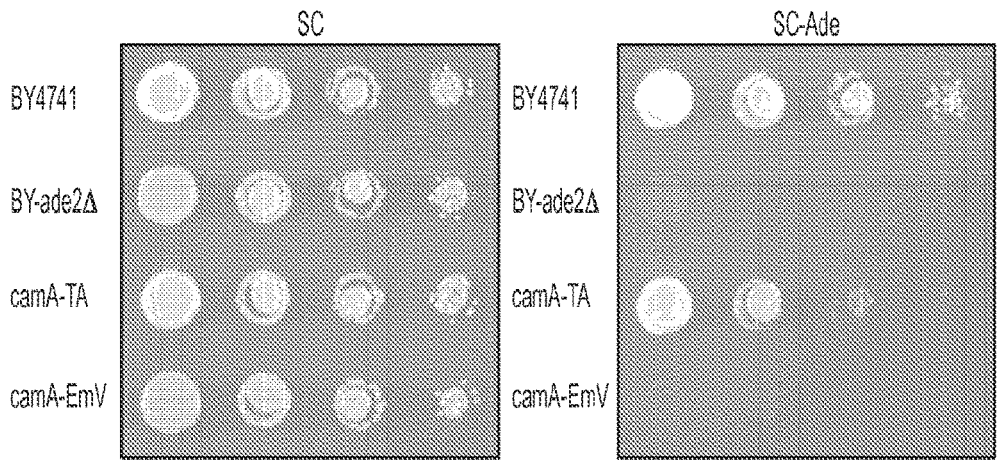
FIG. 4. Camphor responsive ADE2-reporter. Cells were cultured for 1 day at 30° C. in SC (A), SC-Ade (B), SC with 100 µM of camphor (C), and SC-Ade with 100 µM of camphor (D). The cells were 10-fold diluted in across each row.
Figures 4C, 4D:
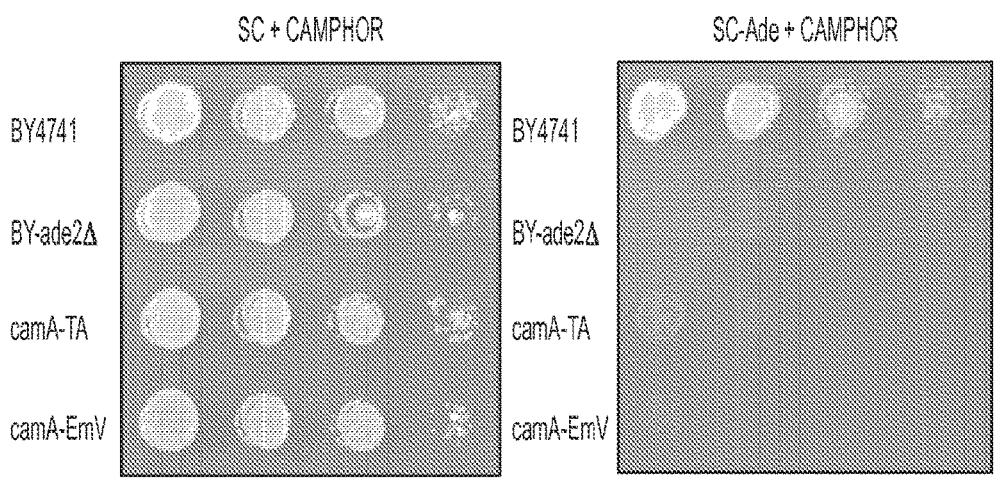

Another gene ADE2 (SEQ ID No. 10) was used to further evaluate the camphor-Off system. Specifically, we investigated availability of the system to complement the adenine-auxotrophy in a camphor-dependent manner. When cam-TA was not expressed in a strain that had camPr-controlled ADE2 gene (SEQ ID No. 10), the strain named camA-EmV grew in SC medium but not in SC-Ade medium irrespective of camphor addition (FIG. 4). On the other hand, another strain camA-TA, which had cam-TA differently from camA-EmV, grew in camphor-free SC-Ade media (FIG. 4B). By contrast, the strain hardly proliferated at all on SC-Ade media that contained camphor (FIG. 4D). The reversion frequency is approximately $10^{-3}$. The behavior of each strain was thoroughly consistent with the schematic model of the camphor-system (FIG. 2). The result showed that the new system constructed in this study was useful for tight regulation of two different genes in yeast.

Growth Effects of Camphor Treatment

Figure 5A:
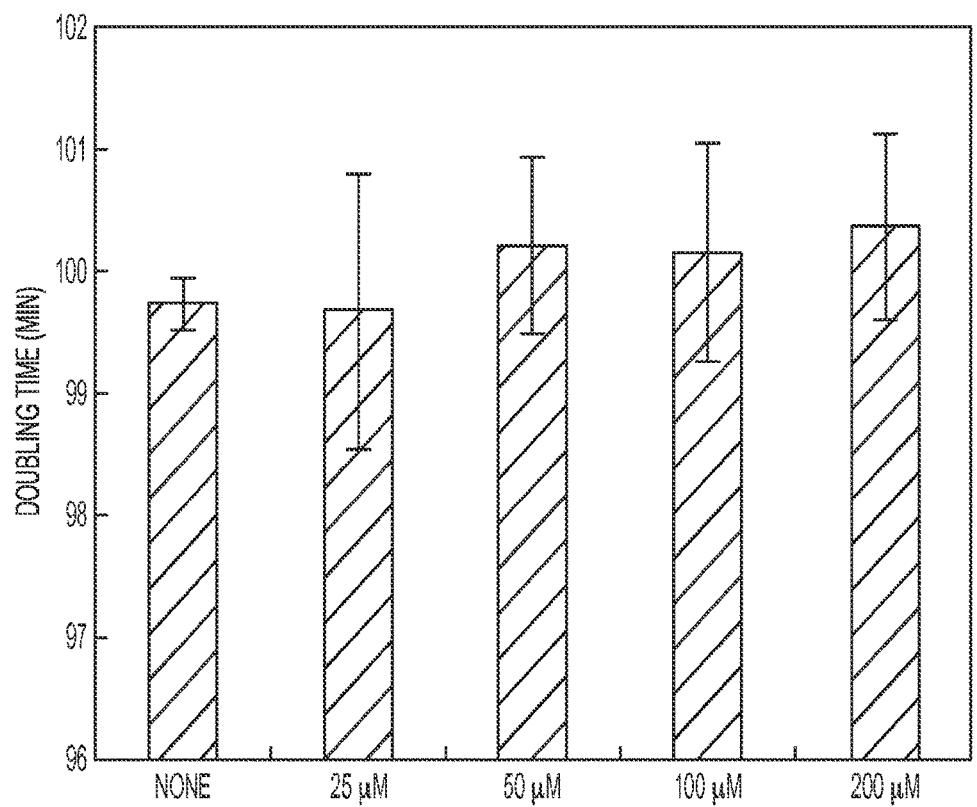
FIG. 5. Effects of camphor on the growth of BY4741 strain. Doubling time in the presence of various concentrations of camphor. The values are means and standard deviations calculated from eight experiments.
Figure 5B:
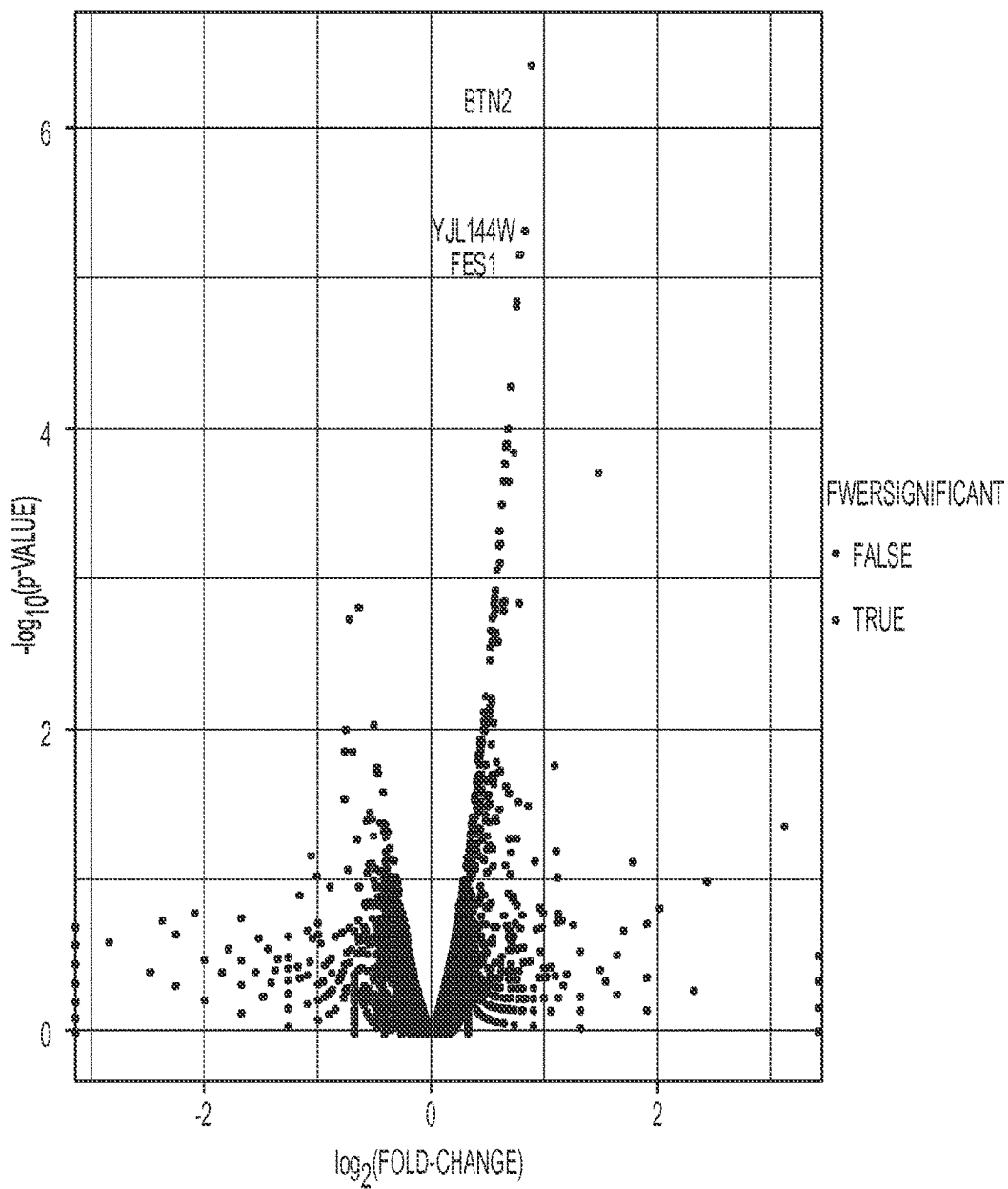

The effective concentration for the camphor-Off system was found to be 25 μM in the previous experiment (FIG. 3). Based on this, we investigated how yeast cells were affected by camphor. When the doubling time of BY4741 was determined quantitatively in five different concentrations of camphor (none, 25 μM, 50 μM, 100 μM, and 200 μM), there was no significant difference between the conditions (FIG. 5).

Orthogonality: Two Different Off Switches in a Single Strain

The experiments in this section were performed to examine whether the camphor-Off system was orthogonal/compatible with the Tet-Off system in a yeast strain. Firstly, we developed new two acceptor vectors: one was used for the camphor-Off switch and the other was the Tet-Off switch. The plasmids were designed to make it easy to clone genes of interest at a BsmBI gap with yeast Golden Gate assembly (FIG. 6AB) and deliver the relevant transcription unit and its transactivator in a single simple step. Here, the mCherry and GFP genes were used as reporters in the camphor- and Tet-Off systems, respectively. When a strain BY-TeCaOFF in which both the systems were integrated was grown lacking both camphor and doxycycline (Dox), significant expression of both fluorescent proteins was observed (FIG. 6C). Moreover, the addition of either drug resulted in drastic decrease of a corresponding reporter protein, while the other fluorescence was detected robustly (FIG. 6DE). In accordance with those data, expression of both the reporters was repressed when both camphor and Dox were supplied in media (FIG. 6F). These results indicated that it was possible to regulate genes separately with the two systems in a single strain.

Example 1

Materials and Methods

Media

Yeast strains were cultured in YPD medium or SD-based media supplemented with appropriate amino acids; fully supplemented medium is referred to as SC; SC missing one component, e.g. adenine, would be labeled SC-Ade. D-Camphor was purchased from Sigma-Aldrich (St. Louis, Mo.), and 5-fluoroorotic acid (5-FOA) was from US Biological (Massachusetts, Mass.). Besides, doxycycline (Dox) was obtained from Clontech laboratories (Mountain View, Calif.). *Escherichia coli* was grown in Luria Broth (LB) media. In order to select strains with drug-resistant genes, carbenicillin (Sigma-Aldrich), kanamycin (Sigma-Aldrich), or zeocin (Life Technologies, Carlsbad, Calif.) were used at final concentrations of 75 μg/ml, 50 μg/ml, and 25 μg/ml respectively. Agar was added to be 2% for preparing agar-media.

Plasmids

The TOP10 strain of *E. coli* (F⁻ mcrAΔ(mrr-hsdRMS-mcrBC) Φ80lacZΔM15 ΔlacX74 recA1 araD139 Δ(araleu) 7697 galUgalKrpsL (StrR) endA1 nupG) was used for the construction and amplification of plasmids.

Figure 7A:
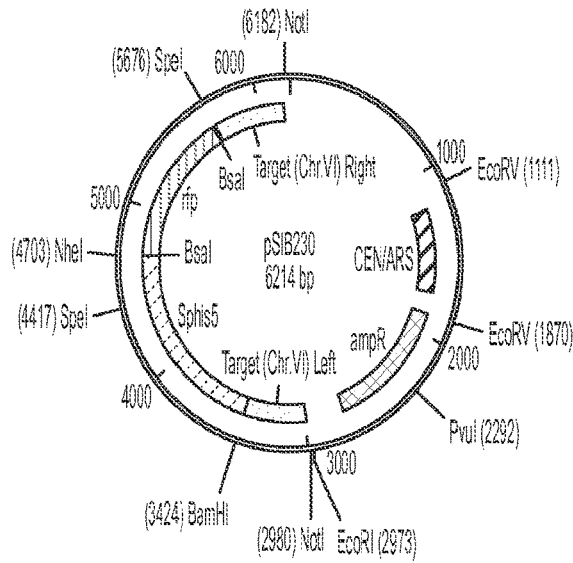
FIG. 7. Acceptor vectors (see FIG. 8) that have rfp gene flanked by BsaI recognition sequence. (A) pSIB230. An integration target of this plasmid was an intergenic region between GAT1/YFL021W and PAU5/YFL020C. (B) pSIB233. A dubious gene, YKL162c-a, was the integration target of the plasmid. (C) pSIB843. The integration target of this plasmid is the HO gene which is nonfunctional in most laboratory yeast strains. All plasmid maps were drawn with SnapGene Viewer (GSL Biotech, Chicago, Ill.).
Figure 7B:
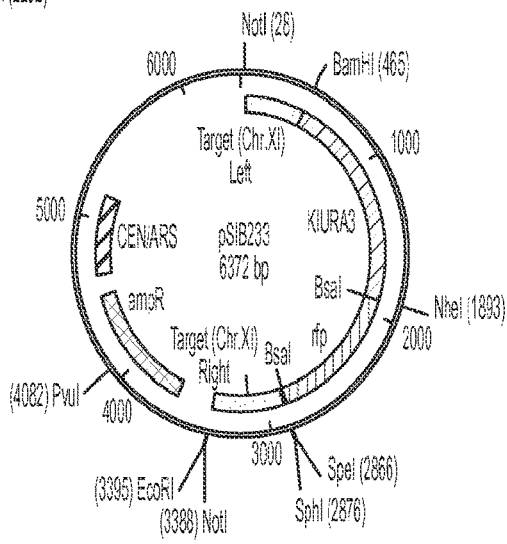
Figure 7C:
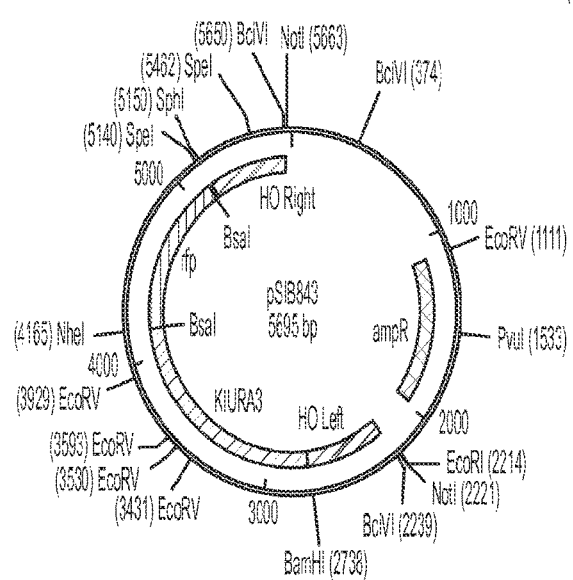
Figure 8:
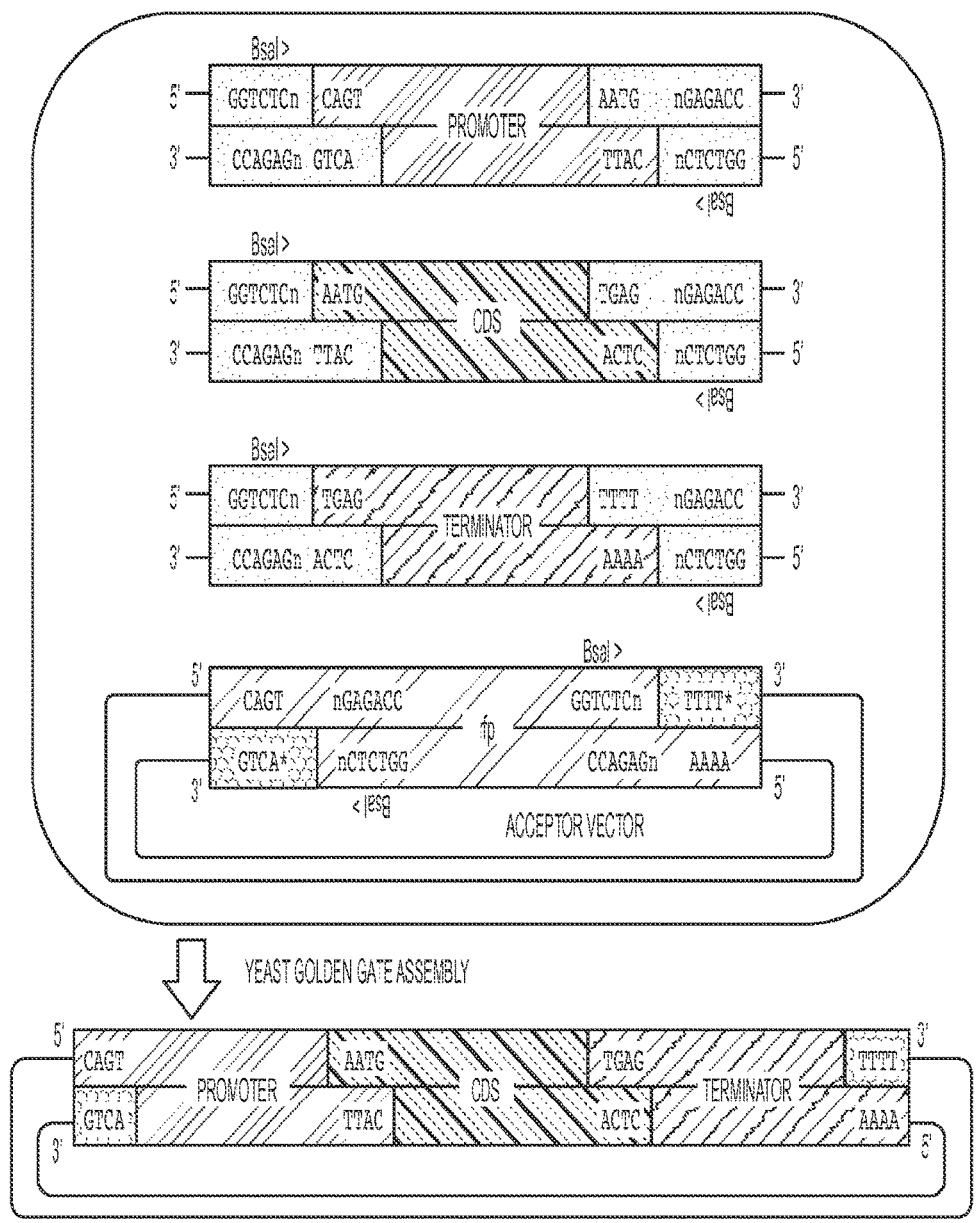
FIG. 8. Schematic diagram of yeast Golden Gate assembly (yGG). Type IIS restriction enzyme BsaI was used to yield sticky ends that ligate with each other. In this study, plasmids called acceptor vectors that were used for the backbone plasmids in yGG reaction had rfp gene flanked by convergent BsaI sites. The overhang sequences for ligating with other DNA fragments were marked with asterisks*. In order to replace the rfp gene with three DNA fragments [a promoter, a coding sequence (CDS), and a terminator], the fragments had nonpalindromic sticky ends that were generated by digestion with BsaI, unless otherwise described.

Plasmids pSIB230, pSIB233, and pSIB843 (FIG. 7) were designed for use with the yeast Golden Gate assembly method (yGG, FIG. 8) which was developed based on previously described methods. In the yGG, Type II restriction enzymes such as BsaI and BsmBI are used to generate sticky ends that ligate with one another in a predetermined order and directionality. Plasmids pSIB230 and 233 are "convertible", meaning they can be used either as a CEN (single copy, episomal) plasmid directly, or, upon cutting with NotI, for integration at chromosomes VI, XI, or IV at sites empirically determined to be non-deleterious to yeast growth. The plasmids were constructed with protocols described previously, and the plasmids were used as "acceptor" vectors in which the rfp gene in them turned the host *E. coli* colonies bright red, facilitating the identification of plasmids with inserts, which make white colonies. The CEN plasmid containing the TDHpr-camTA-STR1tr expression cassette, pSIB619 was made by yGG as follows. The rfp gene in pSIB233 was replaced with the TDH1 promoter (TDH1pr), the coding sequence (CDS) for cam-TA, and STR1 terminator (STR1tr) to construct pSIB619 (FIGS. 1 (A) and (B)). Similarly, the GFP reporter plasmid pSIB426 was built from pSIB230, camPr (as described below), the gfp CDS, and the GSH1 terminator (SEQ ID No. 9). A second ADE2 reporter plasmid, pSIB791, was constructed in which the ADE2 CDS (SEQ ID No. 10). was cloned in place of gfp in the above yGG reaction.

The specialized acceptor vector pSIB859, which is "yGG-ready" for putting any gene under cam-TA control in yeast in an integrated state (at the HO gene on Chr. IV) in one step was constructed as follows. The TDH1pr(v1) part described in the section above consists of a native TDH1 yGG part, but in order to sequentially incorporate two yGG cassettes TDH1pr(v2) was constructed. It consists of the same native promoter part but with a pair of BsmBI sites, ready to accommodate a second TU ("transcription unit") cassette, engineered into the left end. The rfp gene in acceptor vector pSIB843 was replaced with TDH1pr(v2), the cam-TA CDS, and STR1tr. Upon BsmBI digestion of the resulting plasmid it was possible to insert the camPr, rfp, and SOL3 terminator parts using the yGG to generate pSIB859 (FIG. 6A). pSIB859 has a cassette of TDH1 promoter named TDH1pr (v2) (SEQ ID No. 11); Two divergent BsmBI sites lie adjacent to the BsaI site. The overhang produced by the BsmBI sites can be used for the next yGG reaction. pSIB859 also has a rfp gene (CDS) that had BsaI sites at both ends (SEQ ID No. 12). Another type II restriction enzyme BsmBI sites located just inside the BsaI sites, which can be used for the next yGG reaction. Finally, the pSIB859 has a SOL3 terminator (SEQ ID No. 13) in which the innate BsmBI recognition sequence was disrupted.

In order to build a combined mCherry reporter/camR-TA plasmid pSIB872, we swapped the rfp gene in pSIB859 with the mCherry gene (SEQ ID No. 14). To make an analogous tet-GFP integrating construct, the rfp gene of pSIB230 was replaced with a similarly engineered (paired BsmBI sites) human CMV promoter from human cytomegalovirus, tTA (consisting of a TetR-VP16 fusion, and the STR1tr) (SEQ ID No. 15 and 16). The resultant plasmid was digested with BsmBI and then ligated to three DNA fragments, tet promoter (tetPr), rfp, and GSH1tr. The tetPr (SEQ ID No. 17) itself consists of three subparts, the ADH1tr, tet operator, and CYC1 minimal promoter. Subsequently, the CEN/ARS region was removed from this plasmid by EcoRV cutting and religation to generate pSIB498 (FIG. 6B). Plasmid pSIB527 was build by replacing rfp of pSIB498 with gfp gene. The construction of pSIB527 has a cassette of CMV promoter from human cytomegalovirus (SEQ ID No. 15). The 5'-side of BsaI site was followed by two BsmBI sites. The gap of the BsmBI can be used for the next yGG reaction. Plasmid pSIB527 also has a sequence of tTA (CDS) that consists of TetR (1-618) and VP16 (619-747) (SEQ. ID No. 16). Finally, Plasmid pSIB527 has a sequence of a promoter (tetPr) (SEQ ID No. 17) consisting of ADH1 terminator (1-207), TetR operator (216-508), and CYC1 minimal promoter (521-667).

Yeast Strains

Yeast strains are listed in Table 1. Particularly, strain BY-ade2Δ was constructed as follows: BY4741 was transformed with BamHI-digested pAADE2 followed by the selection of Ura⁺ colonies, and then Ura⁻ Ade⁻ derivatives were subsequently identified by screening for Ade⁻ colonies after selection on SC+100 μg/ml 5-FOA medium. The other strains were constructed by integrating the expression cassettes that were prepared by digesting the aforementioned pSIB-series of plasmids with NotI and selecting for the appropriate marker. Yeast cells were cultured at 30° C.

TABLE 1

Yeast strains used in this study.

| Strain | Alternate name | Genotype | Source |
| --- | --- | --- | --- |
| BY4741 | | MATa his3Δ1 leu2Δ0 met15Δ0 ura3Δ0 | Laboratory stock |
| camG | SIY504 | BY4741 targetChVI*::pSIB426 (Sphis5, camPr-gfp) | This study |
| camG-TA | SIY733 | BY4741 targetChVI::pSIB426 (Sphis5, camPr-gfp) ykl162c::pSIB619 (KlURA3, camTA) | This study |
| BY-ade2Δ | SIY390 | BY4741 ade2Δ::hisG (derived from pΔADE2) | This study |
| camA-TA | SIY794 | BY-ade2Δ targetChVI::pSIB791 (Sphis5, camPr-ADE2) ykl1262c::pSIB619 (KlURA3, camTA) | This study |
| camA-EmV | SIY795 | BY-ade2Δ targetChVI::pSIB791 (Sphis5, camPr-ADE2) ykl162c::pSIB233 (KlURA 3) | This study |
| BY4742 | | MATalpha his3Δ1 leu2Δ0 lys2Δ0 ura3Δ0 | Laboratory stock |
| TetOffG | SIY555 | BY4742 targetChVI::pSIB527 (Sphis5, tetPr-gfp, tTA) | This study |
| BY-TeCaOFF | SIY797 | BY4742 ho::pSIB872 (KlURA3, camPr-rfP, camTA) targetChVI::pSIB527 (Sphis5, tetPr-gfp, tTA) | This study |

*targetChVI: an intergenic region between GAT1/YFL021W and PAU5/YFL020C.

Flow Cytometry

Cellular fluorescence from GFP was determined using a LSRII flow cytometer (Becton Dickinson, Franklin Lakes, N.J.) equipped with 488-nm argon ion laser (blue laser) and a 530/30-filter. All samples were suspended in sterile water, and 10,000 cells were analyzed per sample. Data acquisition and analysis were performed using FACSDiva software (Becton Dickinson) and FlowJo (Tree Star, Ashland, Oreg.).

Growth Tests

Yeast growth was monitored using an Eon Microplate Spectrophotometer with Gen5 software (BioTek, Winooski, Vt.), and 96 Well Clear Flat Bottom plates (Corning, N.Y.)

were used to culture the cells. Fresh cells were suspended in the required medium, and then 200 µl of the samples were filled in each well. Typically, the initial value of $A_{600}$ was 0.20 to 0.25, and the absorbance was measured at 600 nm every 10 minute. Doubling time was determined from cells that were in logarithmic phase.

Microscopy

Cells were viewed with an Axioskop-2 microscope (Carl Zeiss, Oberkochen, Germany) equipped with an X-cite120 light source (ExFo, Ontario, Canada) and a fluorescence filter set. A 100× objective and AxioVision software were used to capture fluorescence and differential interference contrast (DIC) images.

A person of ordinary skill would understand that the present system can be used in multiple industrial applications. For example, the system can be utilized for the large scale fermentation of yeast producing pharmaceuticals, including biologics and biosimilars applications. The company would have a yeast strain suitable for industrial expression of the molecule(s) of interest at hand, containing all genes but one (typically this would be the first gene in the pathway) under the control of previously optimized constitutive promoters. Then, the critical gene (or the only gene in the case of production of a single protein) could be placed under the control of the camPr (camphor regulated promoter). For example, a seed culture of yeast containing a gene of interest under the control of the camPr as well as the cam-TA expression construct described here, would be grown up in the presence of 25 µM camphor in the appropriate yeast growth medium such as YPD, or minimal (e.g. SD) medium. The volume of the seed culture might be 1 L for a 100 L fed-batch fermentor or 100 L for a 10,000 L fermentor, or 10,000 L for a 1,000,000 L fermentor. The seed culture would then be diluted 1:100 into medium lacking camphor, causing growth of the yeast and, simultaneously, expression of the protein of interest. Alternatively, the yeast could be diluted into such medium containing an empirically determined optimal concentration of camphor, if lower levels of expression were more desirable for optimal production.

In other embodiments, the system can be used for large scale fermentation of yeast producing biofuels. The company would have a yeast suitable for industrial expression of the fuel molecule(s) of interest at hand, containing all genes but one (typically this would be the first gene in the pathway) under the control of previously optimized constitutive promoters. Then, the critical gene could be placed under the control of the camPr (camphor regulated promoter). For example, a seed culture of yeast containing a gene of interest under the control of the camPr as well as the camTA expression construct described here, would be grown up in the presence of 25 µM camphor in the appropriate yeast growth medium such as YPD, or minimal (e.g. SD) medium. The volume of the seed culture might be 1 L for a 100 L fed-batch fermentor or 100 L for a 10,000 L fermentor, or 10,000 L for a 1,000,000 L fermentor. The seed culture would then be diluted 1:100 into medium lacking camphor, causing growth of the yeast and, simultaneously, expression of the protein of interest. Alternatively, the yeast could be diluted into such medium containing an empirically determined optimal concentration of camphor, if lower levels of expression were more desirable for optimal production.

In yet a further embodiment, the system can be utilized for small or large scale fermentation of yeast producing any recombinant protein.

The system described herein may also be utilized for biological circuit components in yeast or other species in which the camphor switch-off system is implemented. For example, it is possible to produce Boolean "logic gates" control using small molecules. One such gate, the NOR gate, is considered universal because using a series of NOR gates linked together in various ways, one can produce any other type of logic gate.

A NOR gate conforms to a logic table indicated below

| INPUT | | OUTPUT |
|---|---|---|
| A | B | A NOR B |
| 0 | 0 | 1 |
| 0 | 1 | 0 |
| 1 | 0 | 0 |
| 1 | 1 | 0 |

A simple example of a biological NOR gate is one in which a pathway's expression is under the control of two small molecules, such as doxycycline and camphor. Consider a three step pathway A-B-C in which all three proteins are required to make product molecule P. In the example below the presence of a compound is indicated by a one (1) and its absence by a zero (0). If the expression of the A protein is controlled by doxycycline and the B protein is controlled by camphor, then production of product P requires the absence of both doxycycline and camphor. This might be desirable if the product P is particularly toxic to cells but the intermediates in the pathway were not, as it would afford tighter "dual control" of the product. In the presence of either compound alone, very little if any P would be made, but in the absence of both the pathway would be maximally expressed.

The well-known tetracycline controlled switch comes in two formats, Tet-OFF, and Tet-ON; where OFF and ON relates to the expression logic of the target gene in the presence of the ligand (doxycycline or tetracycline). All of the above examples relate to a Camphor-OFF switch format, in which the presence of camphor leads to repression of a gene. Using the methods described to develop the Tet-ON system (Braselmann et al. 1993), it may be possible to isolate a Camphor-ON system.

INDUSTRIAL APPLICABILITY

This invention relates to the field of biotechnology and more specifically to a system and method for control of gene expression in eukaryotic cells. The method and devices described herein can be made and practiced in industry in the field of biotechnology.

REFERENCES

The following references are incorporated herein by reference in their entirety.

Aparicio, O. M., B. L. Billington and D. E. Gottschling, 1991 Modifiers of position effect are shared between telomeric and silent mating-type loci in *S. cerevisiae*. Cell 66: 1279-1287.

Aramaki, H., Y. Sagara, M. Hosoi and T. Horiuchi, 1993 Evidence for autoregulation of camR, which encodes a repressor for the cytochrome P-450cam hydroxylase operon on the *pseudomonas putida* CAM plasmid. J. Bacteriol. 175: 7828-7833.

Aramaki, H., H. Kabata, S. Takeda, H. Itou, H. Nakayama et at, 2011 Formation of repressor-inducer-operator ternary complex: Negative cooperativity of $_D$-camphor binding to CamR. Genes Cells 16: 1200-1207.

Baron, U., M. Gossen and H. Bujard, 1997 Tetracycline-controlled transcription in eukaryotes: Novel transactivators with graded transactivation potential. Nucleic Acids Res. 25: 2723-2729.

Braselmann, S., Graninger, P., and Busslinger, M., 1993 A selective transcriptional induction system for mammalian cells based on Gal-4-estrogen receptor fusion proteins. Proc. Natl. Acad. Sci. U.S.A. 90: 1657-1661.

Engler, C., and S. Marillonnet, 2011 Generation of families of construct variants using golden gate shuffling. Methods Mol. Biol. 729: 167-181.

Fujita, M., H. Aramaki, T. Horiuchi and A. Amemura, 1993 Transcription of the cam operon and camR genes in *pseudomonas putida* PpG1. J. Bacteriol. 175: 6953-6958.

Gari, E., L. Piedrafita, M. Aldea and E. Herrero, 1997 A set of vectors with a tetracycline-regulatable promoter system for modulated gene expression in *saccharomyces cerevisiae*. Yeast 13: 837-848.

Kalderon, D., B. L. Roberts, W. D. Richardson and A. E. Smith, 1984 A short amino acid sequence able to specify nuclear location. Cell 39: 499-509.

Maya, D., M. J. Quintero, M. de la Cruz Munoz-Centeno and S. Chavez, 2008 Systems for applied gene control in *saccharomyces cerevisiae*. Biotechnol. Lett. 30: 979-987.

Mitchell, L. A., Y. Cai, M. Taylor, A. M. Noronha, J. Chuang et at, 2013 Multichange isothermal mutagenesis: A new strategy for multiple site-directed mutations in plasmid DNA. ACS Synth. Biol. 2: 473-477.

Richardson, S. M., S. J. Wheelan, R. M. Yarrington and J. D. Boeke, 2006 GeneDesign: Rapid, automated design of multikilobase synthetic genes. Genome Res. 16: 550-556.

Tsuge, K., K. Matsui and M. Itaya, 2003 One step assembly of multiple DNA fragments with a designed order and orientation in *bacillus subtilis* plasmid. Nucleic Acids Res. 31: e133.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive. All references cited herein are incorporated by reference in their entireties.

What is claimed is:

1. A system comprising for controlling expression of a gene of interest in yeast comprising:
   (a) a first plasmid comprising (i) an operon for camphor repressor (camR); and (ii) a gene of interest downstream of the operon for camR; and
   (b) a second plasmid comprising (i) a nucleotide sequence encoding camR,
   wherein, in the absence of camphor, camR binds to the camR operon and drives expression of the gene of interest, and
   wherein, in the presence of camphor, camR does not bind to the camR operon and the gene of interest is not expressed.

2. The system of claim 1, wherein the first plasmid further comprises a transcription terminator sequence.

3. The system of claim 2, wherein the transcription terminator sequence is located upstream of the camR operon.

4. The system of claim 2, wherein the transcription terminator sequence comprises an alcohol dehydrogenase ADH1 terminator.

5. The system of claim 1, wherein the camR operon comprises SEQ ID NO:18.

6. The system of claim 1, wherein the first plasmid comprises at least six copies of the camR operon.

7. The system of claim 1, wherein the second plasmid further comprises a transcriptional activation domain.

8. The system of claim 7, wherein the transcriptional activation domain comprises a VP16 tandem repeat.

9. The system of claim 1, wherein the second plasmid further comprises a nuclear localization signal.

10. The system of claim 9, wherein the nuclear localization signal is derived from SV40.

11. The system of claim 1, wherein the second plasmid further comprises a glycolytic promoter sequence.

12. The system of claim 11, wherein the glycolytic promoter sequence is TDH1.

13. The system of claim 1, wherein the first plasmid further comprises a promoter downstream from the camR operon.

14. The system of claim 13, wherein the promoter lacks an upstream activating sequence.

15. The system of claim 14, wherein the promoter is CYC1.

* * * * *

SEQUENCE LISTING

```
<160> NUMBER OF SEQ ID NOS: 18

<210> SEQ ID NO 1
<211> LENGTH: 7258
<212> TYPE: DNA
<213> ORGANISM: Artificial Sequence
<220> FEATURE:
<223> OTHER INFORMATION: Synthetic sequence

<400> SEQUENCE: 1
gtcaccaccc tgccctttttt ctttaaaacc gaaaagatta cttcgcgtta tgcaggcttc      60
ctcgctcact gactcgctgc gctcggtcgt tcggctgcgg cgagcggtat cagctcactc     120
aaaggcggta atacggttat ccacagaatc agggggataac gcaggaaaga acatgtgagc     180
aaaaggccag caaaaggcca ggaaccgtaa aaaggccgcg ttgctggcgt ttttccacag     240
gctccgcccc cctgacgagc atcacaaaaa tcgacgctca agtcagaggt ggcgaaaccc     300
gacaggacta taaagatacc aggcgtttcc ccctggaagc tccctcgtgc gctctcctgt     360
tccgaccctg ccgcttaccg gatacctgtc cgcctttctc ccttcgggaa gcgtggcgct     420
ttctcatagc tcacgctgta ggtatctcag ttcggtgtag gtcgttcgct ccaagctggg     480
ctgtgtgcac gaaccccccg ttcagcccga ccgctgcgcc ttatccggta actatcgtct     540
tgagtccaac ccggtaagac acgacttatc gccactggca gcagccactg gtaacaggat     600
tagcagagcg aggtatgtag gcggtgctac agagttcttg aagtggtggc ctaactacgg     660
ctacactaga agaacagtat ttggtatctg cgctctgctg aagccagtta ccttcggaaa     720
aagagttggt agctcttgat ccggcaaaca aaccaccgct ggtagcggtg gttttttttgt     780
```

```
ttgcaagcag cagattacgc gcagaaaaaa aggatctcaa gaagatcctt tgatcttttc      840
tacggggtct gacgctcagt ggaacgaaaa ctcacgttaa gggattttgg tcatgagatt      900
atcaaaaagg atcttcacct agatcctttt aaattaaaaa tgaagtttta aatcaatcta      960
aagtatatat gagtaaactt ggtctgacag ctcgaggctt ggattctcac caataaaaaa     1020
cgcccggcgg caaccgagcg ttctgaacaa atccagatgg agttctgagg tcattactgg     1080
atctatcaac aggagtccaa gcgagctcga tatcaaatta cgccccgccc tgccactcat     1140
cgcagtactg ttgtaattca ttaagcattc tgccgacatg gaagccatca caaacggcat     1200
gatgaacctg aatcgccgga cggatcgctt gcctgtaact tacacgcgcc tcgtatcttt     1260
taatgatgga ataatttggg aatttactct gtgtttattt atttttatgt tttgtatttg     1320
gattttagaa agtaaataaa gaaggtagaa gagttacgga atgaagaaaa aaaaataaac     1380
aaaggtttaa aaaattcaa caaaaagcgt actttacata tatatttatt agacaagaaa     1440
agcagattaa atagatatac attcgattaa cgataagtaa aatgtaaaat cacaggattt     1500
tcgtgtgtgg tcttctacac agacaagatg aaacaattcg gcattaatac ctgagagcag     1560
gaagagcaag ataaaaggta gtatttgttg gcgatccccc tagagtcttt tacatcttcg     1620
gaaaacaaaa actatttttt ctttaatttc ttttttttact ttctattttt aatttatata     1680
tttatattaa aaaatttaaa ttataattat ttttatagca cgtgatgaaa aggacccagg     1740
tggcactttt cggggaaatg tgcgcggaac ccctatttgt ttattttttct aaatacattc     1800 aaatatgtat ccgctcatga gacaataacc ctgataaatg cttcaataat attgaaaaag     1860
gaagagtgat atcatgagta ttcaacattt ccgtgtcgcc cttattccct tttttgcggc     1920
attttgcctt cctgtttttg ctcacccaga aacgctggtg aaagtaaaag atgctgaaga     1980
tcagttgggt gcacgagtgg gttacatcga actggatctc aacagcggta agatccttga     2040
gagttttcgc cccgaagaac gttttccaat gatgagcact tttaaagttc tgctatgtgg     2100
cgcggtatta tcccgtattg acgccgggca agagcaactc ggtcgccgca tacactattc     2160
tcagaatgac ttggttgagt actcaccagt cacagaaaag catcttacgg atggcatgac     2220
agtaagagaa ttatgcagtg ctgccataac catgagtgat aacactgcgg ccaacttact     2280
tctgacaacg atcggaggac cgaaggagct aaccgctttt ttgcacaaca tgggggatca     2340
tgtaactcgc cttgatcgtt gggaaccgga gctgaatgaa gccataccaa acgacgagcg     2400
tgacaccacg atgcctgtag caatggcaac aacgttgcgc aaactattaa ctggcgaact     2460
acttactcta gcttcccggc aacaattaat agactggatg gaggcggata agttgcagg      2520 accacttctg cgctcggccc ttccggctgg ctggtttatt gctgataaat ctggagccgg     2580
tgagcgtgga tctcgcggta tcattgcagc actggggcca gatggtaagc cctcccgtat     2640
cgtagttatc tacacgacgg ggagtcaggc aactatggat gaacgaaata gacagatcgc     2700
tgagataggt gcctcactga ttaagcattg gtaatttctc catttagct tccttagctc      2760 ctgaaaatct cgataactca aaaaatacgc ccggtagtga tcttatttca ttatggtgaa     2820
agttggaacc tcttacgtgc ccgatcaact cgagtgccac ctgacgtcta agaaaccatt     2880
attatcatga cattaaccta aaaaatagg cgtatcacga ggcagaattt cagataaaaa       2940
aaatccttag ctttcgctaa ggatgatttc tggaattcgc ggccgcgtat ccttgcttct     3000
ttatttggca gcattttca aaaataataa aatggaagcc gcgagtacga acaatgatgt      3060
gttctgggaa tacctcgtca aaacaagaca atggcaagga ttttctttca tcaggcagaa     3120
agatctggat ctgaatggca tcattttgtg atgtgtaaaa gcgggacctt gttatttcga     3180
```

```
cttttttgcat catgttgatg caatttgcta cttttccgac ggtgcgctcc aacggatggg    3240
tatttcctta ataacaaggc atttctctgg aagttggctt actgtttgaa atcacagccg    3300
gtcacaaaat aaagtaaaaa aactatctct ctccacaaga agtaattaca ggttgtatac    3360
tacatatgat cgtatttctt tatgaacact aaggagtttc ccgctgtgta ccgcaatagc    3420
cacggatcct gtttagcttg cctcgtcccc gccgggtcac ccggccagcg acatggaggc    3480
ccagaatacc ctccttgaca gtcttgacgt gcgcagctca ggggcatgat gtgactgtcg    3540
cccgtacatt tagcccatac atccccatgt ataatcattt gcatccatac attttgatgg    3600
ccgcacggcg cgaagcaaaa attacggctc ctcgctgcag acctgcgagc agggaaacgc    3660 tccccctcaca gacgcgttga attgtcccca cgccgcgccc ctgtagagaa atataaaagg    3720
ttaggatttg ccactgaggt tcttctttca tatacttcct tttaaaatct tgctaggata    3780
cagttctcac atcacatccg aacataaaca accatgggta ggagggcttt tgtagaaaga    3840
aatacgaacg aaacgaaaat cagcgttgcc atcgctttgg acaaagctcc cttacctgaa    3900
gagtcgaatt ttattgatga acttataact tccaagcatg caaaccaaaa gggagaacaa    3960
gtaatccaag tagacacggg aattggattc ttggatcaca tgtatcatgc actggctaaa    4020
catgcaggct ggagcttacg actttactca agaggtgatt taatcatcga tgatcatcac    4080
actgcagaag atactgctat tgcacttggt attgcattca agcaggctat gggtaacttt    4140
gccggcgtta aaagatttgg acatgcttat tgtccacttg acgaagccct tctagaagc    4200 gtagttgact tgtcgggacg gccctatgct gttatcgatt tgggattaaa gcgtgaaaag    4260
gttggggaat tgtcctgtga aatgatccct cacttactat attccttttc ggtagcagct    4320
ggaattactt tgcatgttac ctgcttatat ggtagtaatg accatcatcg tgctgaaagc    4380
gcttttaaat ctctggctgt tgccatgcgc gcggctacta gtcttactgg aagttctgaa    4440
gtcccaagca cgaagggagt gttgtaaaga gtactgacaa taaaaagatt cttgttttca    4500
agaacttgtc atttgtatag ttttttttata ttgtagttgt tctattttaa tcaaatgtta    4560
gcgtgattta tattttttttt cgcctcgaca tcatctgccc agatgcgaag ttaagtgcgc    4620
agaaagtaat atcatgcgtc aatcgtatgt gaatgctggt cgctatactg ctgtcgattc    4680
gatactaacg ccgccatcca gtgctagcag tcacttctaa ataagcgaat ttcttatgat    4740
ttatgatttt tattattaaa taagttataa aaaaaataag tgtatacaaa ttttaaagtg    4800
actcttaggt tttaaaacga aaattcttgt tcttgagtaa ctctttcctg taggtcaggt    4860
tgctttctca ggtatagcat gaggtcgctc ttattgacca cacctctacc ggcaaggtca    4920
ggctctatat ctgcgatata ctgagcatat cccccccagg ctctatatct gcgatatact    4980
gagcatatcc ccccaggct ctatatctgc gatatactga gcatatcccc ccaggctct    5040 atatctgcga tatactgagc atatcccccc aggctctata tctgcgatat actgagcata    5100
tccccccagg ctctatatct gcgatatact gagcatatcc caatggcatg catgtgctct    5160
gtatgtatat aaaactcttg ttttcttctt ttctctaaat attctttcct tatacattag    5220
gtcctttgta gcataaatta ctatacttct atagacacgc aaaacacaaat acacacacta    5280 aattaataat ggtgagcaag ggcgaggagc tgttcaccgg ggtggtgccc atcctggtcg    5340
agctggacgg cgacgtaaac ggccacaagt tcagcgtgag gggcgaaggc gagggcgatg    5400
ccaccaacgg caagctgacc ctgaagttca tctgcaccac cggcaagctg cccgtgccct    5460
ggcccaccct cgtgaccacc ttgacctacg gcgtgcagtg cttcgcccgc taccccgacc    5520
```

| | | |
|---|---|---|
| acatgaagca gcacgacttc ttcaagtccg ccatgcccga aggctacgtc caggagcgca | 5580 | |
| ccatcttctt caaggacgac ggcacctaca agacccgcgc cgaggtgaag ttcgagggcg | 5640 | |
| acaccctggt gaaccgcatc gagctgaagg gcatcgactt caaggaggac ggcaacatcc | 5700 | |
| tggggcacaa gctggagtac aactacaaca gccacaaggt ctatatcacc gccgacaagc | 5760 | |
| agaagaacgg catcaaggtg aacttcaaga tccgccacaa cgtggaggac ggcagcgtgc | 5820 | |
| agctcgccga ccactaccag cagaacaccc ccatcggcga cggccccgtg ctgctgcccg | 5880 | |
| acaaccacta cctgagcacc cagtccgtgc tgagcaaaga ccccaacgag aagcgcgatc | 5940 | |
| acatggtcct gctggagttc gtgaccgccg ccgggatcac tctcggcatg gacgagctgt | 6000 | |
| acaagtaatg agactccttt tacttcggtt gtgaaagaaa gttgacatta tcgatttggg | 6060 | |
| tgacacggtg attgaaaaag caacgaccag tattatacct ctttttttta ttattcagtt | 6120 | |
| tatattttg caagtgatct taagcatttc tacacaaact tatgccaacg tgaccattta | 6180 | |
| ttattttata tagcaaaaaa aaatgagggg ccttgcagaa caattgttgc gagtttctaa | 6240 | |
| taacaagcac gtagaatatt ggccatttaa ttttctctt caatttatag aatggttgtg | 6300 | |
| ttagtgacaa aaagaatatt cttccccgcc aggactcgaa cctggaatct cctggttcgt | 6360 | |
| agccagacgc cgtgaccatt gggccacgag gaacaagaat ataaagatct ctgagggcaa | 6420 | |
| ggtatgccta tgtcgcaata aaatgtttgt tcctgcgcaa aagtaaagtt ctattaatat | 6480 | |
| acaactacac agtatcggt tcacactatt cgatagttgt aaaaaccatt ttgataaaga | 6540 | |
| tataacaagg cgtttattaa ggacattttt gctacaagtc gtgaagtatt gattgtaggc | 6600 | |
| gatcgttggt aactttctcc atatcggaat attcaatatt gaactcaccc ctcccttgcg | 6660 | |
| ataagctcct tagcttattg gtgtaggtgg taatttccct tagtggcact ttcgctttta | 6720 | |
| ctagtgcatg cagaaacttc tgtggcttga cagataaata actgcagtag tcggtgcgta | 6780 | |
| ctaattgttt ggtcgtgtct gaaaaatctt gaattttcag aaaagaataa gccccaaatg | 6840 | |
| tcagtgatgg tagtagcagt actcccctac gattttagat actttagaga gcccaccttc | 6900 | |
| agaatcggaa ggaggataat tttgtaaagc ccttctgttt tttctcttgc ataacttata | 6960 | |
| tttccacatc aaaaagtagt gtgctaagaa aaaggtcaca agaaaaagga ttacggcact | 7020 | |
| ctctgcatct agacatatac caaaagttgg gtttgctcac gaaaatacca taattgtggt | 7080 | |
| gtcaaaaaaa tcctgcctca taataccact gcagcaattg tggatgacta aaaaataact | 7140 | |
| tgcattccac gatgttattt tactttataa agcacctgca atttttttt ttgtattaac | 7200 | |
| tcatcgagta tgtctgatgg atacgcggcc gctgcagtcc ggcaaaaaag gcaaggt | 7258 | |

<210> SEQ ID NO 2
<211> LENGTH: 558
<212> TYPE: DNA
<213> ORGANISM: Artificial Sequence
<220> FEATURE:
<223> OTHER INFORMATION: Synthetic sequence

<400> SEQUENCE: 2

| | | |
|---|---|---|
| atggacatca agcaatcttt gttgcacgct gctatgagat tgttgtctgc taagggtcgc | 60 | |
| gacggtgcta ccatgcgacc aatctgtgct gaagttggtg ttaccccacc aaccttgtac | 120 | |
| caccactacg gtgacttgca aggtttgcac aaggctgcta tcgacgaaac ctacagacaa | 180 | |
| gttgctgaag cttaccacgg tggtaccgaa gaaagaggtc cattgaaggg tatccgcgac | 240 | |
| ggttgggcta ccttcttgca attcgcttac tctgaaccaa acatgtgtag aatgttggtt | 300 | |
| caacacatca tggctggtga accaccatct atggttgctg acaccttgag aggtgttgct | 360 | |

```
gacgacttgg ctcaattcca cgctcaaggt agattgacct tcccaccaag agaagctgct    420
caattgttgt ggatgggtgc tttgggtgct ttgacctacg ctttgtctag agaaggtgct    480
ggttacaccc aagacttggc tttgcaaaag gctaagttgg acatcacctt ggttgctttg    540
ttcaacatcg aagaagaa                                                 558

<210> SEQ ID NO 3
<211> LENGTH: 126
<212> TYPE: DNA
<213> ORGANISM: Artificial Sequence
<220> FEATURE:
<223> OTHER INFORMATION: Synthetic sequence

<400> SEQUENCE: 3
gggccggccg acgctttgga cgacttcgac ttggacatgt tgcctgcaga tgcacttgat     60
gattttgatc ttgatatgct tccagcagac gcattggatg actttgacct tgacatgctt    120
cctggt                                                              126

<210> SEQ ID NO 4
<211> LENGTH: 27
<212> TYPE: DNA
<213> ORGANISM: Artificial Sequence
<220> FEATURE:
<223> OTHER INFORMATION: Synthetic sequence

<400> SEQUENCE: 4
atgccaaaga agaagagaaa ggtatga                                        27

<210> SEQ ID NO 5
<211> LENGTH: 860
<212> TYPE: DNA
<213> ORGANISM: Artificial Sequence
<220> FEATURE:
<223> OTHER INFORMATION: Synthetic sequence

<400> SEQUENCE: 5
ctcgatggat tagtttctca caggtaacat aacaaaaacc aagaaaagcc cgcttctgaa     60
aactacagtt gacttgtatg ctaaagggcc agactaatgg gaggagaaaa agaaacgaat    120
gtatatgctc atttacactc tatatcacca tatggaggat aagttgggct gagcttctga    180
tccaatttat tctatccatt agttgctgat atgtcccacc agccaacact tgatagtatc    240
tactcgccat tcacttccag cagcgccagt agggttgttg agcttagtaa aaatgtgcgc    300
accacaagcc tacatgactc cacgtcacat gaaaccacac cgtggggcct tgttgcgcta    360
ggaataggat atgcgacgaa gacgcttctg cttagtaacc acaccacatt ttcaggggt     420 cgatctgctt gcttcctta ctgtcacgag cggcccataa tcgcgctttt tttttaaaag     480
gcgcgagaca gcaaacagga agctcgggtt tcaaccttcg gagtggtcgc agatctggag    540
actggatctt tacaatacag taaggcaagc caccatctgc ttcttaggtg catgcgacgg    600
tatccacgtg cagaacaaca tagtctgaag aaggggggga ggagcatgtt cattctctgt    660
agcagtaaga gcttggtgat aatgaccaaa actggagtct cgaaatcata taaatagaca    720
atatattttc acacaatgag atttgtagta cagttctatt ctctctcttg cataaataag    780
aaattcatca agaacttggt ttgatatttc accaacacac acaaaaaaca gtacttcact    840
aaatttacac acaaaacaaa                                               860

<210> SEQ ID NO 6
```

<211> LENGTH: 730
<212> TYPE: DNA
<213> ORGANISM: Artificial Sequence
<220> FEATURE:
<223> OTHER INFORMATION: Synthetic Sequence

<400> SEQUENCE: 6

| tcgccagtgc catgtttctg ccttcgaccg gacctttta agtacgataa atatcctttt | 60 |
| ataaatatat agtctaaaat atccattaat actgtgctca atcaatcgtg ttagatgatt | 120 |
| tagttttttc caaatcgtta ttatagtgca gaagtagtat acataaaggc atatgcatgc | 180 |
| gatttggaag taacgctcgc cgtagacaag taagaatgcc tgctgtcttg agaaccaggt | 240 |
| ccaaagaatc ctctatagag cagaagcctg cttccagaac tagaacgaga tcaagaaggg | 300 |
| gcaagcgtgg tcgtgacgat gatgatgatg acgacgatga ggaaagcgat gatgcatacg | 360 |
| atgaagtagg taatgactat gacgagtatg cttcaagagc gaagctggcc accaataggc | 420 |
| ccttcgaaat agtcgcggga ctgcctgcta gtgtggagct gcccaactat aactcttcgc | 480 |
| ttactcatcc gcaatcaatt aaaaattctg gggtgcttta cgactctctg gtcagttcca | 540 |
| gaagaacctg ggttcagggt gagatgtttg aactgtattg gcgaagacct aagaaaattg | 600 |
| ttagtgaatc taccccagca gcgacggaga gtccaacatc tggaacgatt cctttgattc | 660 |
| gagataagat gcagaaaatg tgcgattgtg taatgagtgg aggtcctcac acgttcaaag | 720 |
| ttagactttt | 730 |

<210> SEQ ID NO 7
<211> LENGTH: 577
<212> TYPE: DNA
<213> ORGANISM: Artificial Sequence
<220> FEATURE:
<223> OTHER INFORMATION: Synthetic sequence

<400> SEQUENCE: 7

| cacttctaaa taagcgaatt tcttatgatt tatgattttt attattaaat aagttataaa | 60 |
| aaaaataagt gtatacaaat tttaaagtga ctcttaggtt ttaaaacgaa aattcttgtt | 120 |
| cttgagtaac tctttcctgt aggtcaggtt gctttctcag gtatagcatg aggtcgctct | 180 |
| tattgaccac acctctaccg gcaaggtcag gctctatatc tgcgatatac tgagcatatc | 240 |
| cccccaggc tctatatctg cgatatactg agcatatccc ccaggctc tatatctgcg | 300 |
| atatactgag catatccccc ccaggctcta tatctgcgat atactgagca tatcccccca | 360 |
| ggctctatat ctgcgatata ctgagcatat cccccaggc tctatatctg cgatatactg | 420 |
| agcatatccc aatggcatgc atgtgctctg tatgtatata aaactcttgt ttcttctttt | 480 |
| tctctaaata ttctttcctt atacattagg tcctttgtag cataaattac tatacttcta | 540 |
| tagacacgca aacacaaata cacacactaa attaata | 577 |

<210> SEQ ID NO 8
<211> LENGTH: 723
<212> TYPE: DNA
<213> ORGANISM: Artificial Sequence
<220> FEATURE:
<223> OTHER INFORMATION: Synthetic sequence

<400> SEQUENCE: 8

| atggtgagca agggcgagga gctgttcacc ggggtggtgc ccatcctggt cgagctggac | 60 |
| ggcgacgtaa acggccacaa gttcagcgtg aggggcgaag gcgagggcga tgccaccaac | 120 |
| ggcaagctga ccctgaagtt catctgcacc accggcaagc tgcccgtgcc ctggcccacc | 180 |

| | |
|---|---:|
| ctcgtgacca ccttgaccta cggcgtgcag tgcttcgccc gctacccgga ccacatgaag | 240 |
| cagcacgact tcttcaagtc cgccatgccc gaaggctacg tccaggagcg caccatcttc | 300 |
| ttcaaggacg acggcaccta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaag gtctatatca ccgccgacaa gcagaagaac | 480 |
| ggcatcaagg tgaacttcaa gatccgccac aacgtggagg acggcagcgt gcagctcgcc | 540 |
| gaccactacc agcagaacac ccccatcggc gacggccccg tgctgctgcc cgacaaccac | 600 |
| tacctgagca cccagtccgt gctgagcaaa gaccccaacg agaagcgcga tcacatggtc | 660 |
| ctgctggagt tcgtgaccgc cgccgggatc actctcggca tggacgagct gtacaagtaa | 720 |
| tga | 723 |

<210> SEQ ID NO 9
<211> LENGTH: 707
<212> TYPE: DNA
<213> ORGANISM: Artificial Sequence
<220> FEATURE:
<223> OTHER INFORMATION: Synthetic Sequence

<400> SEQUENCE: 9

| | |
|---|---:|
| actccttta cttcggttgt gaaagaaagt tgacattatc gatttgggtg acacggtgat | 60 |
| tgaaaagca acgaccagta ttatacctct tttttttatt attcagttta tattttgca | 120 |
| agtgatctta agcatttcta cacaaactta tgccaacgtg accatttatt attttatata | 180 |
| gcaaaaaaa atgaggggcc ttgcagaaca attgttgcga gtttctaata acaagcacgt | 240 |
| agaatattgg ccatttaatt tttctcttca atttatagaa tggttgtgtt agtgacaaaa | 300 |
| agaatattct tccccgccag gactcgaacc tggaatctcc tggttcgtag ccagacgccg | 360 |
| tgaccattgg ccacgagga acaagaatat aaagatctct gagggcaagg tatgcctatg | 420 |
| tcgcaataaa atgtttgttc ctgcgcaaaa gtaaagttct attaatatac aactacacag | 480 |
| ttatcggttc acactattcg atagttgtaa aaaccatttt gataaagata taacaaggcg | 540 |
| tttattaagg acatttttgc tacaagtcgt gaagtattga ttgtaggcga tcgttggtaa | 600 |
| ctttctccat atcggaatat tcaatattga actcacccct cccttgcgat aagctcctta | 660 |
| gcttattggt gtaggtggta atttccctta gtggcacttt cgctttt | 707 |

<210> SEQ ID NO 10
<211> LENGTH: 1716
<212> TYPE: DNA
<213> ORGANISM: Artificial Sequence
<220> FEATURE:
<223> OTHER INFORMATION: Synthetic sequence

<400> SEQUENCE: 10

| | |
|---|---:|
| atggattcta gaacagttgg tatattagga gggggacaat tgggacgtat gattgttgag | 60 |
| gcagcaaaca ggctcaacat taagacggta atactagatg ctgaaaattc tcctgccaaa | 120 |
| caaataagca actccaatga ccacgttaat ggctcctttt ccaatcctct tgatatcgaa | 180 |
| aaactagctg aaaaatgtga tgtgctaacg attgagatta gcatgttga tgttcctaca | 240 |
| ctaaagaatc ttcaagtaaa catcccaaa ttaaaatttt acccttctcc agaaacaatc | 300 |
| agattgatac aagacaaata tattcaaaaa gagcatttaa tcaaaatgg tatagcagtt | 360 |
| acccaaagtg ttcctgtgga acaagccagt gaaacttccc tattgaatgt tggaagagat | 420 |

```
ttgggttttc cattcgtctt gaagtcgagg actttggcat acgatggaag aggtaacttc      480
gttgtaaaga ataaggaaat gattccggaa gctttggaag tactgaagga tcgtcctttg      540
tacgccgaaa atgggcacc atttactaaa gaattagcag tcatgattgt gagatctgtt       600
aacggtttag tgttttctta cccaattgta gagactatcc acaaggacaa tatttgtgac      660
ttatgttatg cgcctgctag agttccggac tccgttcaac ttaaggcgaa gttgttggca      720
gaaaatgcaa tcaaatcttt tcccggttgt ggtatatttg gtgtggaaat gttctattta      780
gaaacagggg aattgcttat taacgaaatt gccccaaggc ctcacaactc tggacattat      840
accattgatg cttgcgtcac ttctcaattt gaagctcatt tgagatcaat attggatttg      900
ccaatgccaa agaatttcac atctttctcc accattacaa cgaacgccat tatgctaaat      960
gttcttggag acaaacatac aaaagataaa gagctagaaa cttgcgaaag agcattggcg     1020
actccaggtt cctcagtgta cttatatgga aaagagtcta gacctaacag aaaagtaggt     1080
cacataaata ttattgcctc cagtatggcg gaatgtgaac aaaggctgaa ctacattaca     1140
ggtagaactg atattccaat caaaatctct gtcgctcaaa agttggactt ggaagcaatg     1200
gtcaaaccat tggttggaat catcatggga tcagactctg acttgccggt aatgtctgcc     1260
gcatgtgcgg ttttaaaaga ttttggcgtt ccatttgaag tgacaatagt ctctgctcat     1320
agaactccac ataggatgtc agcatatgct atttccgcaa gcaagcgtgg aattaaaaca     1380
attatcgctg gagctggtgg ggctgctcac ttgccaggta tggtggctgc aatgacacca     1440
cttcctgtca tcggtgtgcc cgtaaaaggt tcttgtctag atggagtaga ttctttacat     1500
tcaattgtgc aaatgcctag aggtgttcca gtagctaccg tcgctattaa taatagtacg     1560
aacgctgcgc tgttggctgt cagactgctt ggcgcttatg attcaagtta tacaacgaaa     1620
atggaacagt ttttattaaa gcaagaagaa gaagttcttg tcaaagcaca aaagttagaa     1680
actgtcggtt acgaagctta tctagaaaac aagtga                               1716

<210> SEQ ID NO 11
<211> LENGTH: 905
<212> TYPE: DNA
<213> ORGANISM: Artificial Sequence
<220> FEATURE:
<223> OTHER INFORMATION: Synthetic sequence

<400> SEQUENCE: 11
ggtctcacag tagagacgat ctcacgtctc attttctcga tggattagtt tctcacaggt       60
aacataacaa aaaccaagaa aagcccgctt ctgaaaacta cagttgactt gtatgctaaa      120
gggccagact aatgggagga gaaaagaaaa cgaatgtata tgctcattta cactctatat      180
caccatatgg aggataagtt gggctgagct tctgatccaa tttattctat ccattagttg      240
ctgatatgtc ccaccagcca acacttgata gtatctactc gccattcact tccagcagcg      300
ccagtagggt tgttgagctt agtaaaaatg tgcgcaccac aagcctacat gactccacgt      360
cacatgaaac cacaccgtgg ggccttgttg cgctaggaat aggatatgcg acgaagacgc      420
ttctgcttag taaccacacc acattttcag ggggtcgatc tgcttgcttc ctttactgtc      480
acgagcggcc cataatcgcg cttttttttt aaaaggcgcg agacagcaaa caggaagctc      540
gggtttcaac cttcggagtg gtcgcagatc tggagactgg atctttacaa tacagtaagg      600
caagccacca tctgcttctt aggtgcatgc gacggtatcc acgtgcagaa caacatagtc      660
tgaagaaggg ggggagggagc atgttcattc tctgtagcag taagagcttg gtgataatga      720
ccaaaactgg agtctcgaaa tcatataaat agacaatata ttttcacaca atgagatttg      780
```
tagtacagtt ctattctctc tcttgcataa ataagaaatt catcaagaac ttggtttgat      840
atttcaccaa cacacacaaa aaacagtact tcactaaatt tacacacaaa acaaaatgag      900
agacc                                                                 905

<210> SEQ ID NO 12
<211> LENGTH: 982
<212> TYPE: DNA
<213> ORGANISM: Artificial Sequence
<220> FEATURE:
<223> OTHER INFORMATION: Synthetic Sequence

<400> SEQUENCE: 12
ggtctcaaat gagagacggc ctggctctag tagcgatcta cactagcact atcagcgtta       60
ttaagcaccg gtggagtgac gaccttcagc acgttcgtac tgttcaacga tggtgtagtc      120
ttcgttgtgg gaggtgatgt ccagtttgat gtcggttttg taagcacccg gcagctgaac      180 cggttttta gccatgtagg tggttttaac ttcagcgtcg tagtgaccac cgtcttcag       240 tttcagacgc attttgattt cacctttcag agcaccgtct tccgggtaca tacgttcggt      300
ggaagcttcc caacccatgg tttttttctg cataaccgga ccgtcggacg ggaagttggt      360
accacgcagt ttaactttgt agatgaactc accgtcttgc agggaggagt cctgggtaac      420
ggtaacaaca ccaccgtctt cgaagttcat aacacgttcc catttgaaac cttccgggaa      480
ggacagtttc aggtagtccg ggatgtcagc cgggtgttta acgtaagctt tggaaccgta      540
ctggaactgc ggggacagga tgtcccaagc gaacggcagc ggaccacctt tggtaacttt      600
cagtttagcg gtctgggtac cttcgtacgg acgaccttca ccttcacctt cgatttcgaa      660
ctcgtgaccg ttaacggaac cttccatacg aactttgaaa cgcatgaact ctttgataac      720
gtcttcggag gaagccatct agtatttctc ctctttctct agtatgtgtg aaattgttat      780
ccgctcacaa ttccacacaa catacgagcc ggaagcataa agtgtaaagc ctggggtgcc      840
taatgagtga gctaactcac attaattgcg ttgcgctcac tgcccgcttt ccagtcggga      900
aacctgtcgt gccagctgca ttaatgaatc ggccaacgcg cggggagagg cggtttgcgt      960
attgcgtctc atgagcgaga cc                                              982

<210> SEQ ID NO 13
<211> LENGTH: 551
<212> TYPE: DNA
<213> ORGANISM: Artificial Sequence
<220> FEATURE:
<223> OTHER INFORMATION: Synthetic Sequence

<400> SEQUENCE: 13
aaaagacaca catgcgagct ttcgaacctc agatgctaat attacgtgtt atatatacca       60
aactttataa aatgacatag atattttatg ctgtgatagc tttcctgtta tggagaagct      120
cttcttattc cccctgtcaa cttttcatact cttgtagaat ttccttatg ataggtttat      180 cgcttacgaa tttagacttt gatgtgatgg gtttggcacc tgttctttt ccacaacctt      240 tgcgtgcctc atcaatagcg tttgatctgt cgggaaattt gtatttgtag agtgcatcct      300
tgcacattgt atagacccaa ttacgctctt ctaacaggtt cacgaacgat tttatttcag      360
gaacagagcc gattgtactt tttgaaccta taatgatcag cttggatttg gcccttgtca      420
tggcaacatt gactcttctt agctctttca gcagcgctcc tccatttaat tgagaatttc      480
ttctaaccat ggaaataata atgcactttt tgtcacgacc ttgaaactga tcagcagtca      540
agatctctag c          551

<210> SEQ ID NO 14
<211> LENGTH: 714
<212> TYPE: DNA
<213> ORGANISM: Artificial Sequence
<220> FEATURE:
<223> OTHER INFORMATION: Synthetic sequence

<400> SEQUENCE: 14
atggtttcaa aaggtgaaga agataatatg gctattatta agaatttat gagatttaaa          60
gttcatatgg aaggttcagt taatggtcat gaatttgaaa ttgaaggtga aggtgaaggt         120
agaccatatg aaggtactca aactgctaaa ttgaaagtta ctaaaggtgg tccattacca         180
tttgcttggg atattttgtc accacaattt atgtatggtt caaaagctta tgttaaacat         240
ccagctgata ttccagatta tttaaaattg tcatttccag aaggttttaa atgggaaaga         300
gttatgaatt ttgaagatgg tggtgttgtt actgttactc aagattcatc attacaagat         360
ggtgaattta tttataaagt taaattgaga ggtactaatt ttccatcaga tggtccagtt         420
atgcaaaaaa aaactatggg ttgggaagct tcatcagaaa gaatgtatcc agaagatggt         480
gctttaaaag gtgaaattaa acaaagattg aaattaaaag atggtggtca ttatgatgct         540
gaagttaaaa ctacttataa agctaaaaaa ccagttcaat taccaggtgc ttataatgtt         600
aatattaaat tggatattac ttcacataat gaagattata ctattgttga acaatatgaa         660
agagctgaag gtagacattc aactggtggt atggatgaat tatataaata atga              714

<210> SEQ ID NO 15
<211> LENGTH: 816
<212> TYPE: DNA
<213> ORGANISM: Artificial Sequence
<220> FEATURE:
<223> OTHER INFORMATION: Synthetic sequence

<400> SEQUENCE: 15
ggtctcacag tagagacgat ctcacgtctc attttgagct tggcccattg catacgttgt          60
atccatatca taatatgtac atttatattg gctcatgtcc aacattaccg ccatgttgac         120
attgattatt gactagttat taatagtaat caattacggg gtcattagtt catagcccat         180
atatggagtt ccgcgttaca taacttacgg taaatggccc gcctggctga ccgcccaacg         240
accccccgccc attgacgtca ataatgacgt atgttcccat agtaacgcca atagggactt         300
tccattgacg tcaatgggtg gagtatttac ggtaaactgc ccacttggca gtacatcaag         360
tgtatcatat gccaagtacg ccccctattg acgtcaatga cggtaaatgg cccgcctggc         420
attatgccca gtacatgacc ttatgggact ttcctacttg gcagtacatc tacgtattag         480
tcatcgctat taccatggtg atgcggtttt ggcagtacat caatgggcgt ggatagcggt         540
ttgactcacg gggatttcca agtctccacc ccattgacgt caatgggagt ttgttttggc         600
accaaaatca acgggacttt ccaaaatgtc gtaacaactc cgccccattg acgcaaatgg         660
gcggtaggcg tgtacggtgg gaggtctata taagcagagc tcgtttagtg aaccgtcaga         720
tcgcctgtag acgccatcca cgctgttttg acctccatag aagacaccgg gaccgatcca         780
gcctccgcgg cccgaattaa ttcataatga gagacc                                  816

<210> SEQ ID NO 16
<211> LENGTH: 747
<212> TYPE: DNA
<213> ORGANISM: Artificial Sequence
<220> FEATURE:
<223> OTHER INFORMATION: Synthetic sequence

<400> SEQUENCE: 16

| | | | | | |
|---|---|---|---|---|---|
| atgagtagat | tggacaagtc | taaggttatc | aactctgctt | tggaattgtt | gaacgaagtt | 60 |
| ggtatcgaag | gtttgaccac | cagaaagttg | gctcaaaagt | gggtgttga | acaaccaacc | 120 |
| ttgtactggc | acgttaagaa | caagagagct | tgttggacg | ctttggctat | cgaaatgttg | 180 |
| gacagacacc | acacccactt | ctgtccattg | gaaggtgaat | cttggcaaga | cttcttgaga | 240 |
| aacaacgcta | agtctttcag | atgtgctttg | ctctctcacc | gcgacggtgc | taaggttcac | 300 |
| ttgggaacca | gaccaaccga | aaagcaatac | gaaaccttgg | aaaaccaatt | ggctttcttg | 360 |
| tgtcaacaag | gtttctcttt | ggaaaacgct | ttgtacgctt | tgtctgctgt | tggtcacttc | 420 |
| accttgggtt | gtgttttgga | agaccaagaa | caccaagttg | ctaaggaaga | agagaaaacc | 480 |
| ccaaccaccg | actctatgcc | accattgctc | agacaagcta | tcgaattgtt | cgaccaccaa | 540 |
| ggtgctgaac | cagcttttctt | gttcggtttg | gaattgatca | tctgtggttt | ggaaaagcaa | 600 |
| ttgaagtgtg | aatctggtgg | gccggccgac | gctttggacg | acttcgactt | ggacatgttg | 660 |
| ccagctgacg | ctttggacga | cttcgacttg | gacatgttgc | cagctgacgc | tttggacgac | 720 |
| ttcgacttgg | acatgttgcc | aggttga | | | | 747 |

<210> SEQ ID NO 17
<211> LENGTH: 667
<212> TYPE: DNA
<213> ORGANISM: Artificial Sequence
<220> FEATURE:
<223> OTHER INFORMATION: Synthetic sequence

<400> SEQUENCE: 17

| | | | | | |
|---|---|---|---|---|---|
| cacttctaaa | taagcgaatt | tcttatgatt | tatgattttt | attattaaat | aagttataaa | 60 |
| aaaaataagt | gtatacaaat | tttaaagtga | ctcttaggtt | ttaaaacgaa | aattcttgtt | 120 |
| cttgagtaac | tctttcctgt | aggtcaggtt | gctttctcag | gtatagcatg | aggtcgctct | 180 |
| tattgaccac | acctctaccg | gcaggccggc | ccgggtcgag | tttaccactc | cctatcagtg | 240 |
| atagagaaaa | gtgaaagtcg | agtttaccac | tccctatcag | tgatagagaa | aagtgaaagt | 300 |
| cgagtttacc | actccctatc | agtgatagag | aaaagtgaaa | gtcgagttta | ccactcccta | 360 |
| tcagtgatag | agaaaagtga | aagtcgagtt | taccactccc | tatcagtgat | agagaaaagt | 420 |
| gaaagtcgag | tttaccactc | cctatcagtg | atagagaaaa | gtgaaagtcg | agtttaccac | 480 |
| tccctatcag | tgatagagaa | aagtgaaacc | cgggccggcc | tatggcatgc | atgtgctctg | 540 |
| tatgtatata | aaactcttgt | tttcttcttt | tctctaaata | ttctttcctt | atacattagg | 600 |
| tcctttgtag | cataaattac | tatacttcta | tagacacgca | aacacaaata | cacacactaa | 660 |
| attaata | | | | | | 667 |

<210> SEQ ID NO 18
<211> LENGTH: 30
<212> TYPE: DNA
<213> ORGANISM: Artificial Sequence
<220> FEATURE:
<223> OTHER INFORMATION: Synthetic sequence

<400> SEQUENCE: 18
caggctctat atctgcgata tactgagcat        30